(12) United States Patent
Weissman et al.

(10) Patent No.: US 9,284,604 B2
(45) Date of Patent: Mar. 15, 2016

(54) METHODS OF IDENTIFYING A CELLULAR NASCENT RNA TRANSCRIPT

(71) Applicant: The Regents of the University of California, Oakland, CA (US)

(72) Inventors: Jonathan Weissman, San Francisco, CA (US); Lee Stirling Churchman, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 208 days.

(21) Appl. No.: 13/900,356

(22) Filed: May 22, 2013

(65) Prior Publication Data

US 2014/0030706 A1 Jan. 30, 2014

Related U.S. Application Data

(63) Continuation of application No. PCT/US2011/061970, filed on Nov. 22, 2011.

(60) Provisional application No. 61/416,181, filed on Nov. 22, 2010.

(51) Int. Cl.
  *C12Q 1/68* (2006.01)
  *C07H 21/00* (2006.01)

(52) U.S. Cl.
  CPC ............ *C12Q 1/6869* (2013.01); *C12Q 1/6806* (2013.01); *C12Q 1/6809* (2013.01)

(58) Field of Classification Search
  CPC .................................... C12Q 1/68; C12Q 1/48
  See application file for complete search history.

(56) References Cited

U.S. PATENT DOCUMENTS

| | | | |
|---|---|---|---|
| 5,010,175 A | 4/1991 | Rutter et al. | |
| 5,187,079 A * | 2/1993 | Free et al. | 435/69.1 |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 6,172,218 B1 | 1/2001 | Brënner | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,306,597 B1 | 10/2001 | Macevicz | |
| 6,730,293 B1 | 5/2004 | Rothbard et al. | |
| 6,969,488 B2 | 11/2005 | Bridgham et al. | |
| 7,001,792 B2 | 2/2006 | Sauer et al. | |
| 7,057,026 B2 | 6/2006 | Barnes et al. | |
| 7,115,400 B1 | 10/2006 | Adessi et al. | |
| 7,181,122 B1 | 2/2007 | Levene et al. | |
| 7,211,414 B2 | 5/2007 | Hardin et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,414,163 B1 | 8/2008 | Boldingh et al. | |
| 7,427,673 B2 | 9/2008 | Balasubramanian et al. | |
| 8,859,201 B2 * | 10/2014 | Goldstein | 435/6.1 |
| 2003/0165945 A1 * | 9/2003 | Bird et al. | 435/6 |
| 2004/0018578 A1 * | 1/2004 | Brocia | 435/11 |
| 2005/0042648 A1 | 2/2005 | Griffiths et al. | |
| 2005/0059048 A1 | 3/2005 | Gunderson et al. | |
| 2005/0079510 A1 | 4/2005 | Berka et al. | |
| 2005/0100900 A1 | 5/2005 | Kawashima et al. | |
| 2005/0130173 A1 | 6/2005 | Leamon et al. | |
| 2006/0188901 A1 | 8/2006 | Barnes et al. | |
| 2006/0240439 A1 | 10/2006 | Smith et al. | |
| 2006/0281109 A1 | 12/2006 | Barr Ost et al. | |
| 2007/0166705 A1 | 7/2007 | Milton et al. | |
| 2008/0108082 A1 | 5/2008 | Rank et al. | |
| 2009/0029407 A1 * | 1/2009 | Gazit et al. | 435/30 |
| 2009/0148840 A1 * | 6/2009 | Kanaoka | 435/6 |
| 2009/0214517 A1 * | 8/2009 | Wong et al. | 424/130.1 |

FOREIGN PATENT DOCUMENTS

| | | | |
|---|---|---|---|
| WO | | 91/06678 A1 | 5/1991 |
| WO | | 91/19735 A1 | 12/1991 |
| WO | | 92/00091 A1 | 1/1992 |
| WO | | 93/20242 A1 | 10/1993 |
| WO | | 98/44151 A1 | 10/1998 |
| WO | | 00/18957 A1 | 4/2000 |
| WO | | 02/46456 A1 | 6/2002 |
| WO | 2005/010145 A2 | | 2/2005 |
| WO | 2005/065814 A1 | | 7/2005 |
| WO | 2005/084158 A2 | | 9/2005 |
| WO | 2006/064199 A1 | | 6/2006 |
| WO | 2007/010251 A2 | | 10/2007 |
| WO | 2007/123667 A2 | | 11/2007 |
| WO | 2007/123744 A2 | | 11/2007 |
| WO | 2012/074855 A2 | | 6/2012 |

OTHER PUBLICATIONS

Friedel et al., Metabolic tagging and purification of nascent RNA: implications for transcriptomics. Molecular Biosystems 5 : 1271 (2009).*
Guenther et al., A Chromatin Landmark and Transcription Initiation at Most Promoters in Human Cells. Cell 130 (1) :77 (2007).*
History of Illumina Sequencing downloaded on Mar. 8, 2015 http://www.illumina.com/technology/next-generation-sequencing/solexa-technology.html.*
Kim et al., A High-resolution map of active promoters in the human genome. Nature 436 (7052) : 876 (2005).*
Messmer et al., The global transcriptional maturation program and stimuli-specific gene expression pro® les of human myeloid dendritic cells. International Immunology 15 (4) : 491 (2003).*
Mironov et al., Sensing Small Molecules by Nascent RNA: A Mechanism to Control Transcription in Bacteria. Cell 111 :747 (2002).*
Muse et al., RNA polymerase is poised for activation across the genome. Nat. Geneticvs 39 (12) : 1507 (2007).*

(Continued)

*Primary Examiner* — Ethan Whisenant
(74) *Attorney, Agent, or Firm* — Mintz, Levin, Cohn, Ferris, Glovsky and Popeo, P.C.

(57) ABSTRACT

Methods and compositions for identifying a cellular nascent RNA transcript are provided.

21 Claims, 21 Drawing Sheets

(56) References Cited

OTHER PUBLICATIONS

Schmitt et al.,A rapid and simple method for preparation of RNA from *Saccharomyces cerevisiae*. Nucleic Acids Research 18 (10) : 3091 (1990).*

Siolas et al.,Synthetic shRNAs as potent RNAi triggers Nature Biotechnology 23 (2) : 227 (2005).*

Zeitlinger et al., RNA Polymerase Stalling at Developmental Control Genes in the Drosophila Embryo. Nature Genetics 39 (12) : 1512 (2007).*

Batzer et al., "Enhanced evolutionary PCR using oligonucleotides with inosine at the 3'-terminus", *Nucleic Acid Res.*, vol. 19, pp. 5081 (1991).

Bentley et al., "Accurate whole human genome sequencing using reversible terminator chemistry" *Nature*, vol. 456, pp. 53-59 (2008).

Core et al., "Nascent RNA Sequence Reveals Widespread Pausing and Divergent Initiation at Human Promoters", *Science*, vol. 322, pp. 1845-1848 (2008).

Kim et al., "A high-resolution map of active promoters in the human genome", *Nature*, vol. 436, pp. 876-880 (2005).

Ohtsuka et al., "An Alternative Approach to Deoxyoligonuccleotides as Hybridization Probes by Insertion of Deoxyinosine at Ambiguous Codon Positions*", *The Journal of Biological Chemistry*, vol. 260, pp. 2605-2608 (1985).

Rodriguez-Gil et al., "The distribution of active RNA polymerase II along the transcribed region is gene-specific and controlled by elongation factors", *Nucleic Acids Research*, vol. 38, No. 14, pp. 4651-4664 (2010).

Rossolini et al., "Use of deoxyinosine-containing primers vs degenerate primers for polymerase chain reaction based on ambiguous sequence information", *Mol. Cell Probes*, vol. 8, pp. 91-98 (1994).

Thiebaut et al., "Transcription Termination and Nuclear Degradation of Cryptic Unstable Transcripts: A Role for the Nrd1-Nab3 Pathway in Genome Surveillance", *Molecular Cell*, vol. 23, pp. 853-864 (2006).

Thompson et al., "Cytpplasmic Decay of Integenic Transcripts in *Saccaromyces cerevisiae*", *Mol. Cell. Biol.*, vol. 27, pp. 92-101 (2007).

International Preliminary Report on Patentability and Written Opinion dated May 22, 2013 for International Application No. PCT/US2011/061970, 6 pages.

International Search Report and Written Opinion dated Dec. 27, 2012 for International Application No. PCT/US2011/061970, 11 pages.

Extended European Search Report dated Mar. 19, 2014 for European Application No. EP11844470.2, 6 pages.

* cited by examiner

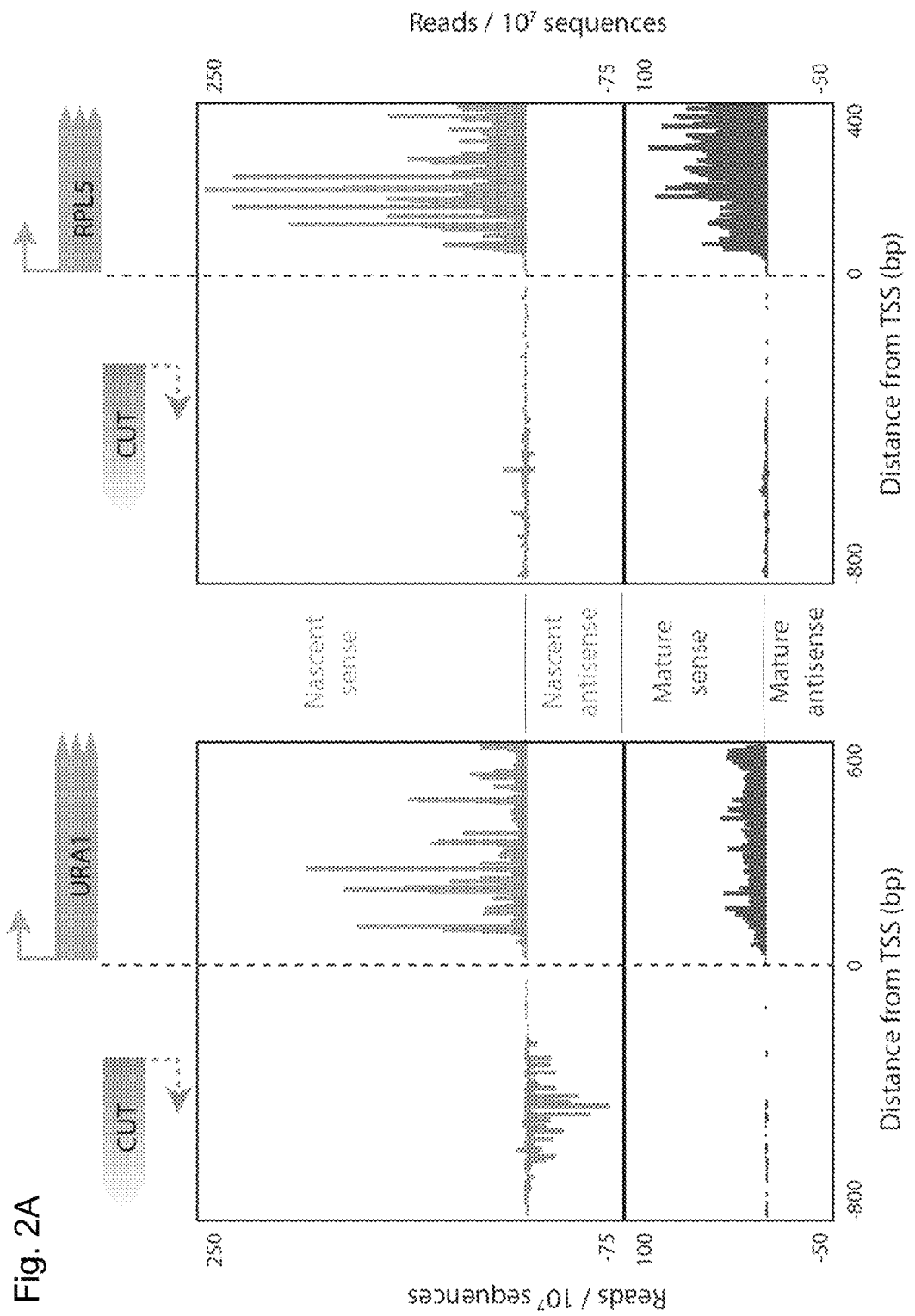

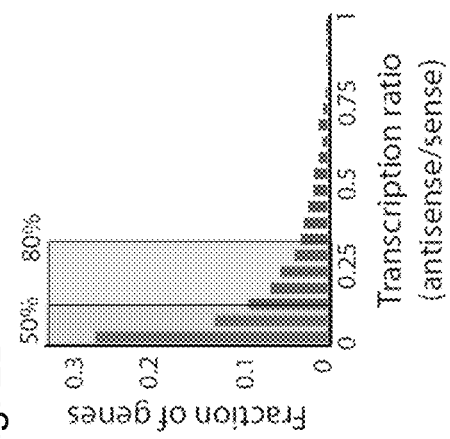
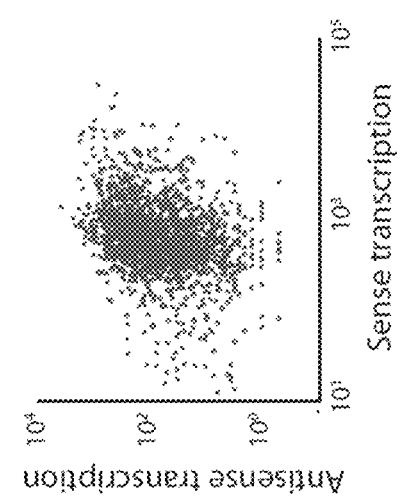
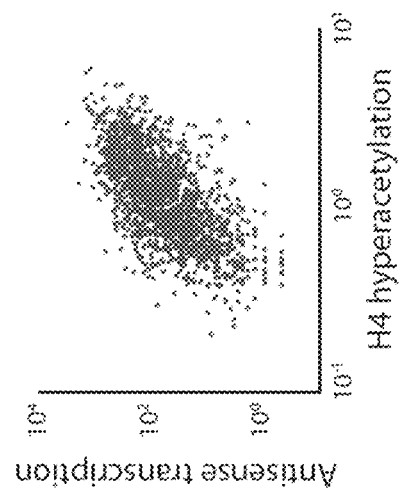
Fig. 2B
Fig. 2C
Fig. 2D

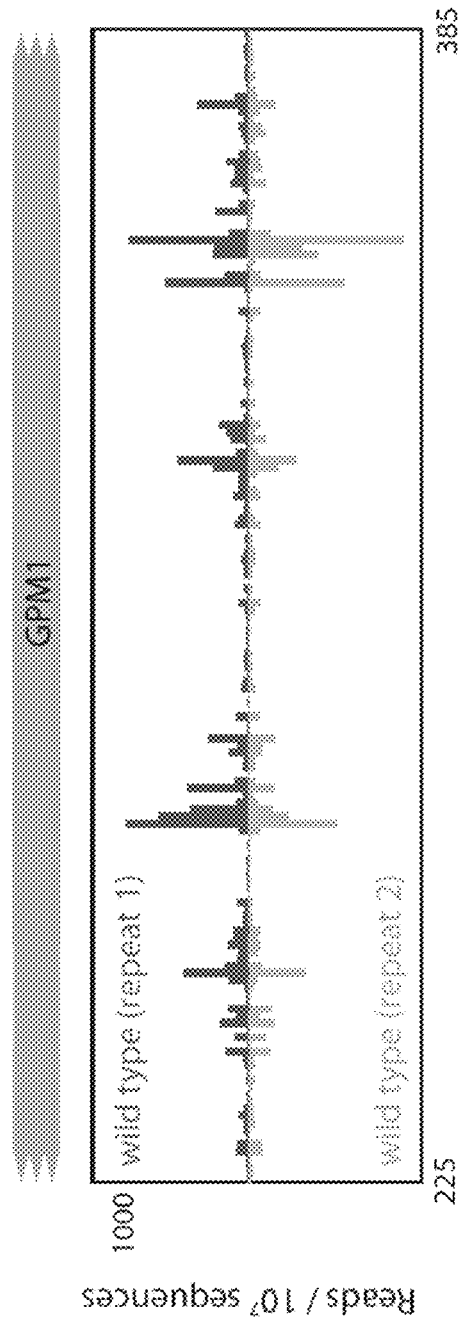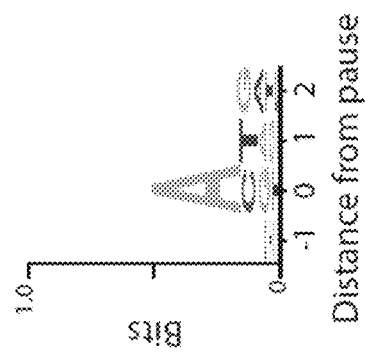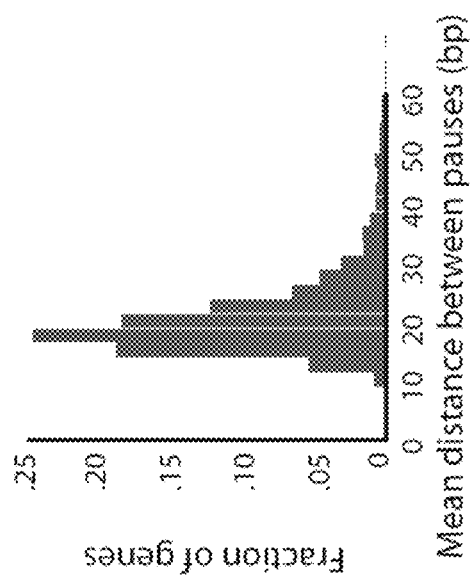
Fig. 4A
Fig. 4B
Fig. 4C

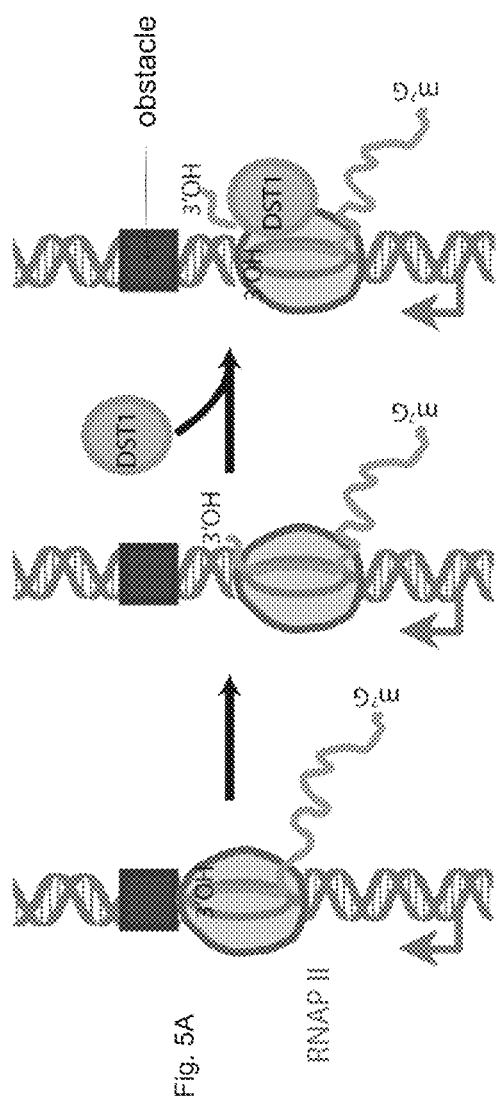
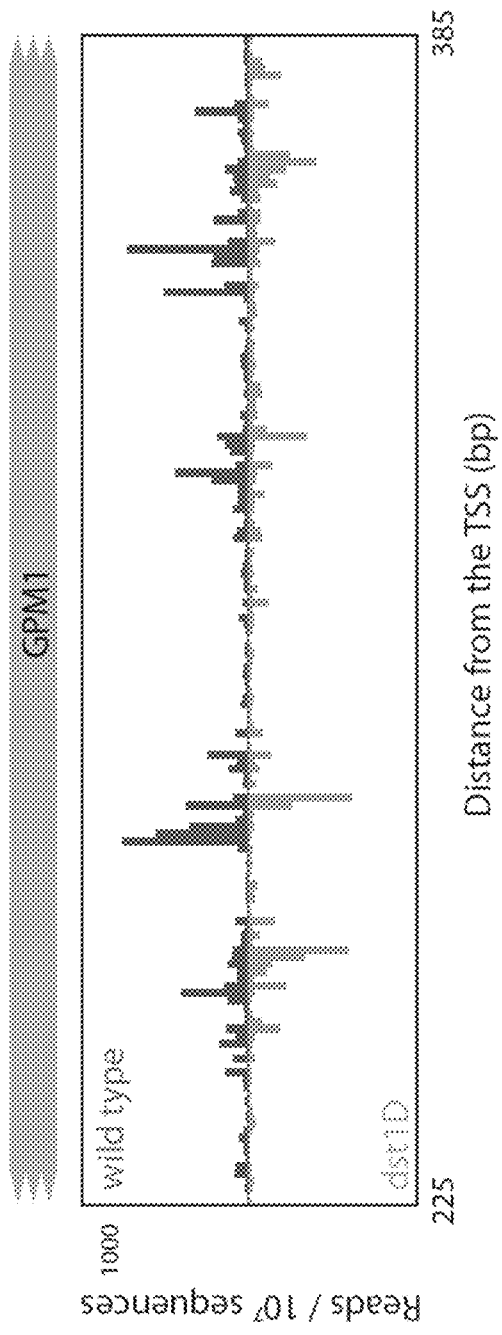
Fig. 5A
Fig. 5B

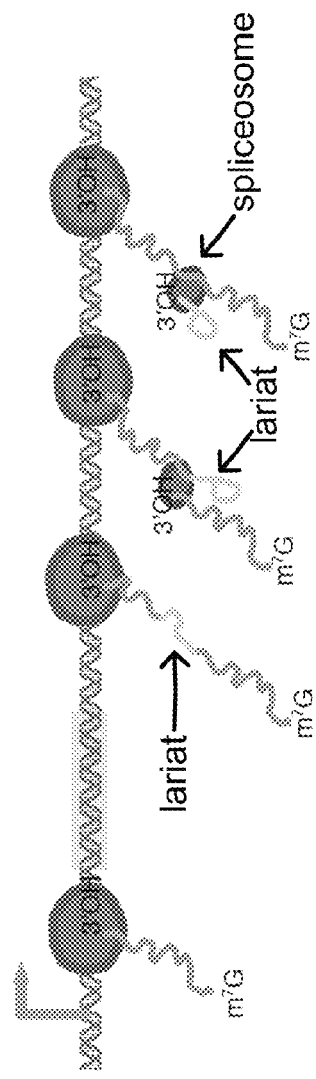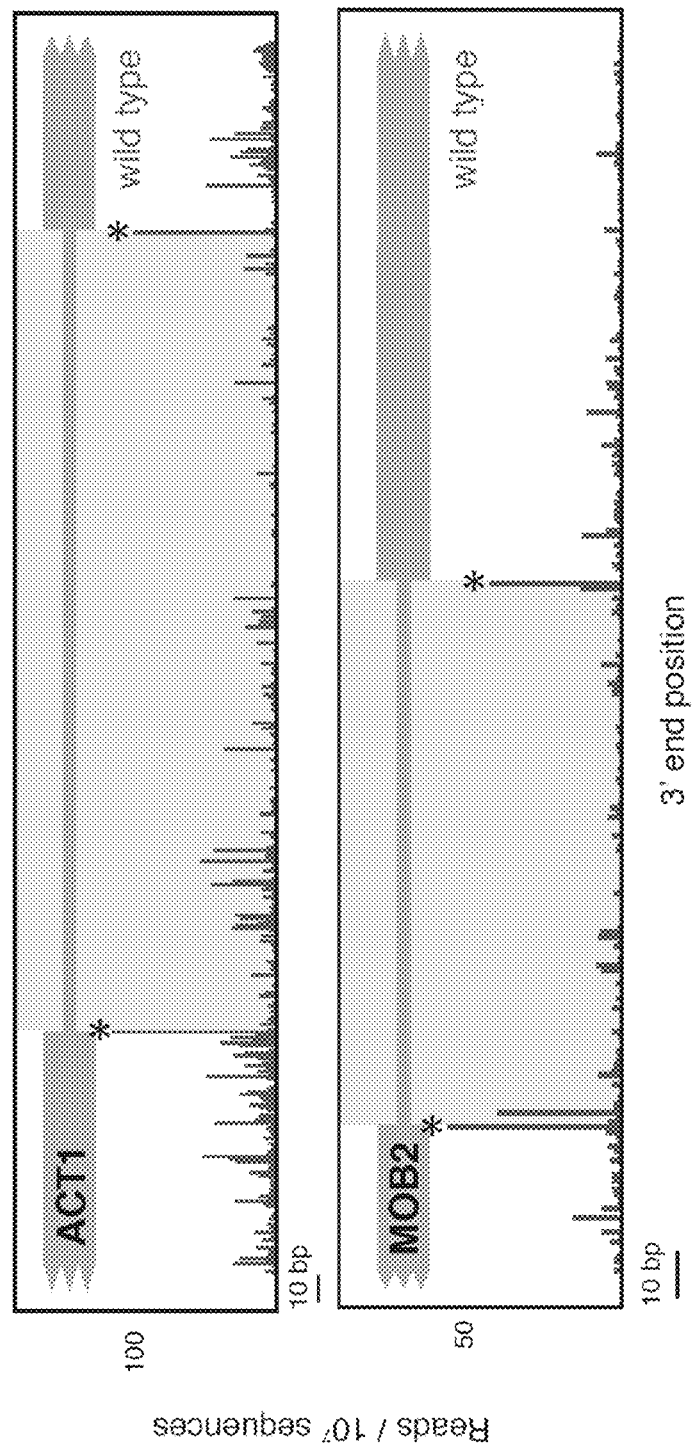
Fig. 8A
Fig. 8B

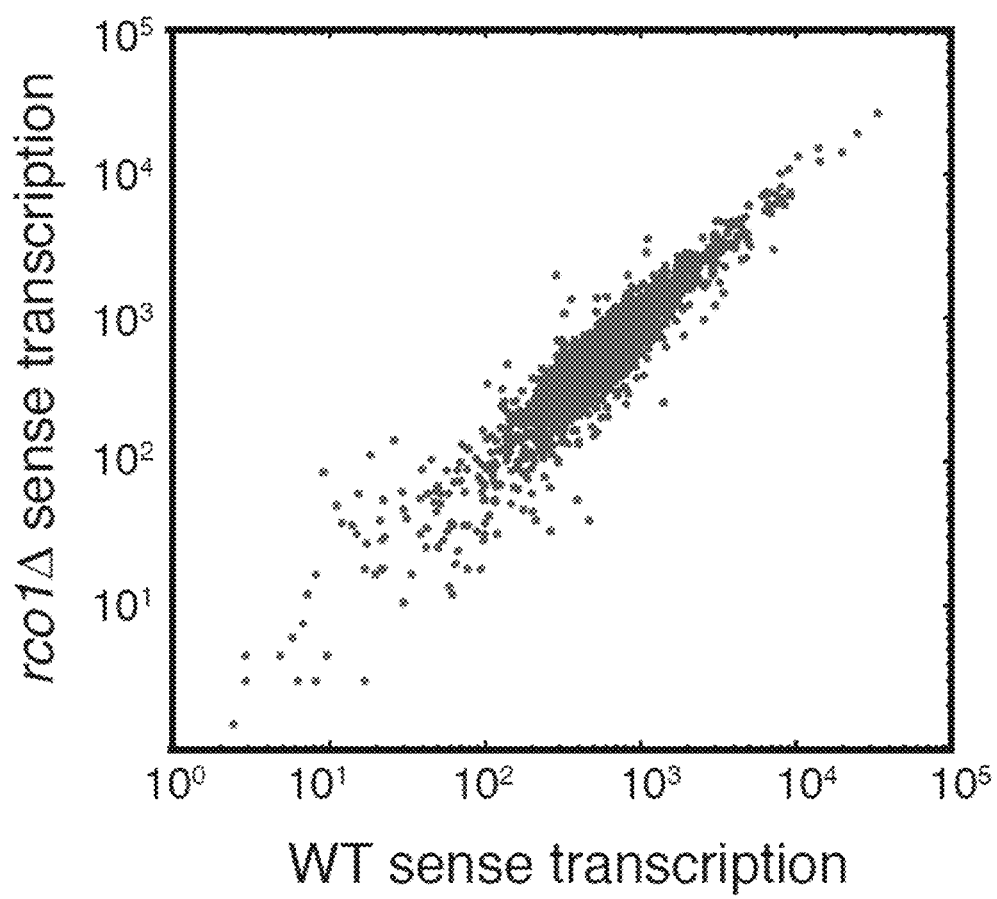

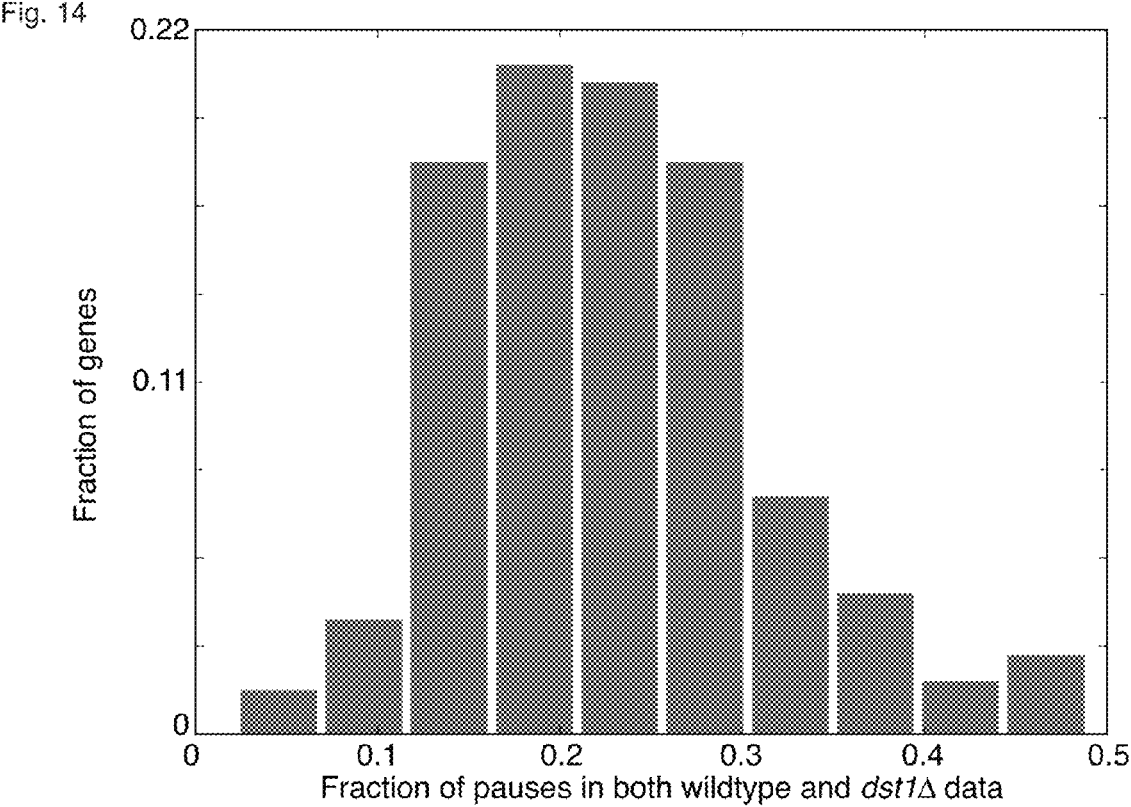

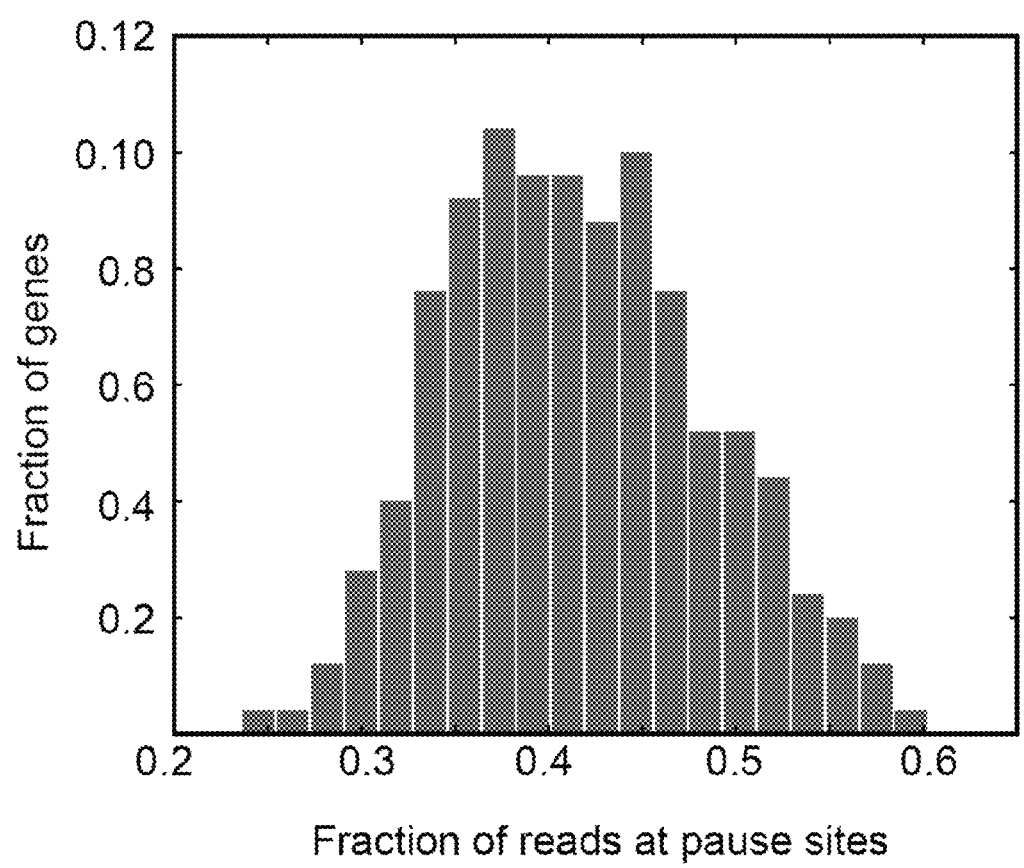

METHODS OF IDENTIFYING A CELLULAR NASCENT RNA TRANSCRIPT

CROSS-REFERENCES TO RELATED APPLICATIONS

This application is a continuation application of PCT Application No. PCT/US2011/061970, filed Nov. 22, 2011, which claims the benefit of U.S. Provisional Appl. No. 61/416,181, filed Nov. 22, 2010, the contents of which are incorporated herein by reference and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 84850-876413_ST25.TXT, created on May 22, 2013, 2,999 bytes, machine format IBM-PC, MS-Windows operating system, is hereby incorporated by reference in its entirety for all purposes.

BACKGROUND OF THE INVENTION

Accumulating evidence now reveals that transcription elongation is not a straightforward read-out of the downstream DNA sequence. Co-transcriptional processing events dictate the covalent nature and fate of RNA transcripts (Moore, M. J. & Proudfoot, N.J. *Cell* 136, 688-700, 2009). Indeed many transcripts are targeted co-transcriptionally for rapid degradation and hence are effectively invisible to approaches that monitor mature messages (Preker, P. et al. *Science* 322, 1851-1854, 2008; Xu, Z. et al. *Nature* 457, 1033-1037, 2009; Neil, H. et al. *Nature* 457, 1038-1042, 2009). In addition to these processing events, the strong propensity of RNAP to pause creates barriers to elongation and provides an opportunity for regulation and coordination of co-transcriptional events (Rougvie, A. E. & Lis, J. T. *Cell* 54, 795-804, 1988; Proshkin, S., et al. *Science* 328, 504-508, 2010). In vitro, RNAP pausing is found to be ubiquitous (Kassayetis, G. A. & Chamberlin, M. J. *J Biol Chem* 256, 2777-2786, 1981). Elegant biophysical approaches have provided a structural and energetic understanding of RNAP pausing which results from both intrinsic properties of the polymerase itself as well as interactions with its DNA template including the presence of bound proteins (e.g. histones) (Shaevitz, J. W., et al. *Nature* 426, 684-687, 2003; Herbert, K. M. et al. *Cell* 125, 1083-1094, 2006; Hodges, C., et al. *Science* 325, 626-628, 2009; Kireeva, M. L. & Kashlev, M. *Proc. Natl. Acad. Sci. USA* 106, 8900-8905, 2009; Kireeva, M. L. et al. *Mol. Cell* 18, 97-108, 2005). In the cell, elongation factors likely alter the energetic landscape of transcription, but the extent and mechanism of RNAP pausing in eukaryotic cells remain largely unknown. Bridging the divide between in vivo and in vitro transcriptional views requires approaches that visualize transcription with comparable precision afforded by in vitro transcriptional assays. More generally, the ability to quantitatively monitor nascent transcripts would provide broad insights into the roles and regulation of transcription initiation, elongation and termination in gene expression.

Historically, two strategies have been used to provide snapshots of transcriptional activity in vivo. In the first approach, RNAP is crosslinked to DNA and RNAP-bound DNA elements are identified by microarrays or deep sequencing (Kim, T. H. et al. *Nature* 436, 876-880 (2005); Lefrançois, P. et al. *BMC genomics* 10, 37 (2009)). While providing a global view of RNAP binding sites, these measurements are of limited spatial and temporal resolution and do not reveal the identity of the transcribed strand or even if RNAP molecules are engaged in transcription. In the second approach, transcription is halted in vivo and then reinitiated in isolated nuclei under conditions that allow labeling of nascent chains thereby enabling them to be distinguished from bulk RNA (Core, L. J., et al. *Science* 322, 1845-1848 (2008); Rodriguez-Gil, A. et al. The distribution of active RNA polymerase II along the transcribed region is gene-specific and controlled by elongation factors. *Nucleic Acids Research* (2010)). Such "nuclear run-on" strategies reveal actively transcribed DNA regions but require extensive manipulations that limit resolution and depend on the efficient reinitiation of transcription under non-physiological conditions.

BRIEF SUMMARY OF THE INVENTION

Provided herein are methods of identifying a native cellular nascent RNA transcript by (a) arresting transcription in a cell; (b) purifying a cellular nascent RNA transcript; and (c) sequencing said cellular nascent RNA transcript thereby identifying the cellular nascent RNA transcript.

BRIEF DESCRIPTION OF THE DRAWINGS

FIG. 1A, Schematic diagram of NET-Seq protocol. A yeast culture is flash frozen and cryogenically lysed. Nascent RNA is co-purified via an immunoprecipitation (IP) of the RNAPII elongation complex. Conversion of RNA into DNA results in a DNA library with the RNA as an insert between DNA sequencing linkers. The sequencing primer is positioned such that the 3' end of the insert is sequenced. m7G refers to the 7-methylguanosine cap structure at the 5' end of nascent transcripts. FIG. 1B, The 3' end of each sequence is mapped to the yeast genome and the number of reads at each nucleotide is plotted at the RPL30 locus for nascent RNA and lightly fragmented mature RNA. Note for the nascent transcripts, the introns (grey box) and regions after the poly-adenylation site (black arrow) are readily detected. FIG. 1C, Metagene analysis for well-expressed genes (N=471, >1.5 reads/bp in both conditions) of the mean read density in the presence (black) and absence (grey) of transcription inhibitor, α-amanitin.

FIG. 2A-2D: Observation of divergent transcripts reveals strong directionality at most promoters. FIG. 2A, Nascent and mature transcripts initiating from URA1 and RPL5 promoters in the sense and antisense directions. Note that there are cryptic unstable transcripts (CUTs) in the antisense direction for URA1 but not RPL5. FIG. 2B, A histogram of the transcription ratio (antisense/sense transcription levels) for 1875 genes. The dark grey left box and light grey right box indicate the subset of genes with a ratio of less than 1:8 and less than 1:3, respectively. FIG. 2C, Antisense transcription levels are plotted versus sense transcription for each tandem gene (Spearman correlation coefficient, $r_s$=0.34). FIG. 2D, The level of antisense transcription for each promoter is plotted versus the local enrichment for H4 hyperacetylation using available data (Pokholok, D. K. et al., *Cell* 122:517-527 (2005)) ($r_s$=0.65).

FIG. 3A, Examples of cryptic unstable transcripts (CUTs, light grey data below CUTs) upstream and antisense of DBF2, DRN1 and VAS1 promoters. The fold increase of CUT transcription in the rco1 Δ strain is marked at bottom. FIG. 3B, The transcription ratio (antisense:sense) in the rco1 Δ strain is plotted against the transcription ratio in the wild type strain for each gene. FIG. 3C, A metagene analysis of well-expressed antisense transcription (N=171, >1 read/bp); wild type (black), rco1D (light grey).

FIG. 4A-4C: Frequent RNAPII pausing throughout gene bodies. FIG. 4A, NET-seq data at the GPM1 gene for biological replicates. FIG. 4B, A histogram of the mean distance between pauses for each well-expressed gene (N=1006, >2 reads/bp). FIG. 4C, The consensus sequence of the DNA coding strand surrounding pause sites found from all genes.

FIG. 5A-5D: Dst1 relieves RNAPII pausing after backtracking FIG. 5A, A schematic describing an existing model for how RNAPII pauses at an obstacle (dark grey square), backtracks and is induced to cleave its transcript through binding to Dst1 (Izban, M. G. & Luse, D. S., *J. Biol. Chem.* 267:13647-13655 (1992); Reines, D. et al., *Current Opinion in Cell Biology* 11:342-346 (1999)). FIG. 5B, A comparison of NET-seq data for wild type and dst1 Δ strains at the GPM1 gene. FIG. 5C, Mean crosscorrelation between the dst1 Δ and wild type data of well transcribed genes (N=770, >2 reads/bp) (light grey line) was calculated by determining the Pearson's correlation coefficient at each gene between fixed dst1 Δ data and shifted wild type data followed by averaging over all genes. This analysis is compared to the mean autocorrelation of the wild type data for well transcribed genes (black line). FIG. 5D, The consensus sequence for all pauses observed in the dst1 Δ strain.

FIG. 8A-8D: Evidence of co-transcriptional splicing in yeast. FIG. 8A, A schematic showing how co-transcriptional splicing intermediates (e.g. spliced exon and excised lariat (light grey)) would remain bound to RNAP II via the spliceosome (small circle). FIG. 8B, Read densities for two spliced genes, ACT1 and MOB2. Note the high densities at their precise exon-intron junctions indicated by stars. FIG. 8C, Average number of reads per base pair for spliced genes versus the gene's reads at the 3' end of splice junctions and FIG. 8D, one base pair downstream from splice junctions; exon (light grey), lariat (black) for FIG. 8C and FIG. 8D.

FIG. 9A-9B) Antisense transcription level versus the width of the promoter's nucleosome free region (NFR) and nucleosome occupancy from available data (Weiner, A. et al., *Genome Res.* 20:90-100 (2010)). R values are Spearman correlation coefficients. FIG. 9C-9D) Antisense transcription level versus H3 acetylation enrichment from available data (Pokholok, D. K. et al., *Cell* 122:517-527 (2005)).

FIG. 10 Comparison between sense transcription in wild type strain and the rco1 Δ strain at divergent promoters. R=0.965, Pearson correlation coefficient. R=0.914, Spearman correlation coefficient.

FIG. 14 Histogram of the fraction of pauses that are found in both wildtype and dst1 Δ data.

FIG. 16 Histogram of the fraction of reads at pause sites for highly-expressed genes (N=256, >10 reads/bp). The reads at all pause sites was summed and then divided by the total number of reads for the gene resulting in the fraction of reads at pause sites.

DETAILED DESCRIPTION OF THE INVENTION

Definitions

Figure 1A:
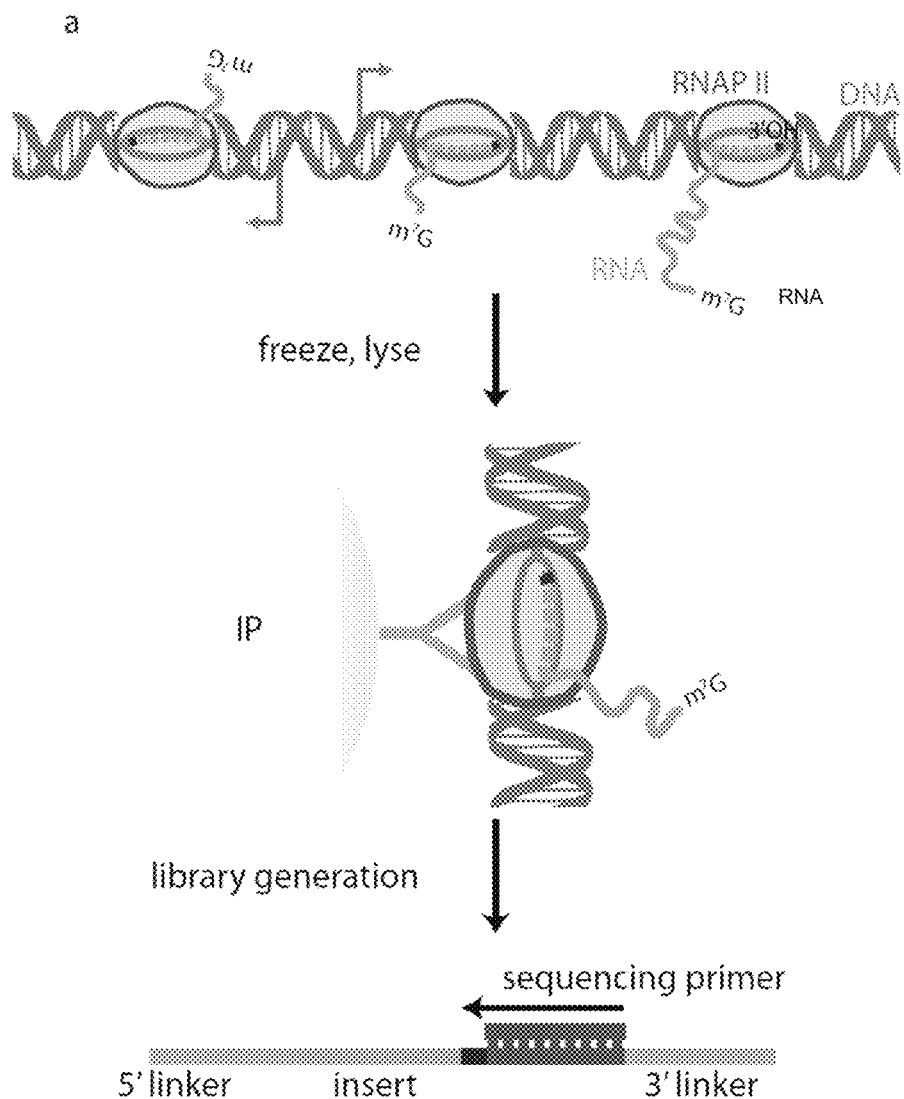
FIG. 1A-1C: NET-seq visualizes active transcription via capture of 3' RNA termini.

As defined herein, the term "transcription" refers to the process by which an RNA molecule is produced from a nucleic acid template. A nucleic acid template may be RNA or DNA.

As defined herein, the term "cellular nascent RNA transcript" refers to an RNA transcript derived from a cell wherein the RNA is associated with a cellular RNA polymerase complex, or a portion thereof. The cellular RNA polymerase complex is a complex of proteins that catalyze the synthesis (polymerization) of the RNA transcript from a nucleic acid template. The term "native RNA transcript" refers to an RNA molecule that does not include a non-native nucleotide (e.g., a non-native ribonucleotide, a labeled nucleotide, or a nucleotide analog).

As defined herein, the term "unstable transcript" refers to any transcript that is unstable or susceptible to degradation by enzymes in a cell, e.g., exosomes or nucleases. In some embodiments, the unstable transcript is a cryptic unstable transcript (see Thompson & Parker, Mol Cell Biol 27:92-101, 2007; Thiebaut et al., Molecular Cell 23:853-864, 2006). In some embodiments, the unstable transcript is a transcript of intergenic regions in the genome. In some embodiments, the unstable transcript is a transcript of genic regions in the genome.

The term "sense strand" is used according to its plain ordinary meaning and refers to a single stranded nucleic acid molecule, (e.g., a single stranded genomic DNA molecule), that is complementary to the DNA strand that is transcribed into RNA, which is subsequently translated into the natural polypeptide product of a gene. The term "antisense strand" is used herein to mean the single strand nucleic acid molecule that is complementary with the sense strand.

The term "antisense DNA" as used herein refers to a DNA molecule that has a nucleotide sequence complementary to the "sense strand" of DNA and that is transcribed into RNA (the "sense transcript") that may be translated into the protein product of a gene. The term "sense DNA" as used herein refers to a DNA molecule that has a nucleotide sequence complementary to the "antisense strand" of DNA. The term "antisense transcript" is used to mean an RNA transcript that is transcribed from a sense strand DNA. An antisense transcript is capable of hybridizing under stringent conditions with a sense strand DNA. In some embodiments, a sense transcript includes a portion of a specific gene transcript (e.g., 5' non-coding region, 3' non-translated sequence, intron, or exon) wherein the gene transcript is transcribed from the antisense strand of DNA, and wherein the exons of such gene transcript may be translated into a protein product of a gene. In some further embodiments, the antisense transcript does not include the complementary transcript to the sense transcript and may not be translated into a protein product of the gene; and the sense transcript and antisense transcript are each transcribed in opposite directions moving away from the same promoter region of DNA. In some embodiments, an antisense transcript may be complementary with any part of a specific gene transcript (sense transcript), i.e., at the 5' non-coding sequence, 3' non-translated sequence, introns, or the coding sequence.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

"Complementary," as used herein, refers to the capacity for precise pairing of two nucleobases (e.g., A to T (or U), and G to C) regardless of where in the nucleic acid the two are located. For example, if a nucleobase at a certain position of nucleic acid is capable of hydrogen bonding with a nucleobase at a certain position of another nucleic acid, then the position of hydrogen bonding between the two nucleic acids is considered to be a complementary position. Nucleic acids are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acids. The phrase "substantially complementary" thus means that there may be one or more mismatches between the nucleic acids when they are aligned, provided that stable and specific binding occurs. The term "mismatch" refers to a site at which a nucleobase in one nucleic acid and a nucleobase in another nucleic acid with which it is aligned are not complementary. The nucleic acids are "perfectly complementary" to each other when they are fully complementary across their entire length.

The phrase "amino acid" as used herein refers to any of the twenty naturally occurring amino acids as well as any modified amino acids. Modifications can include natural processes such as posttranslational processing, or chemical modifications which are known in the art. Modifications include, but are not limited to, phosphorylation, ubiquitination, acetylation, amidation, glycosylation, covalent attachment of flavin, ADP-ribosylation, cross linking, iodination, methylation, and the like.

The words "protein", "peptide", and "polypeptide" are used interchangeably to denote an amino acid polymer or a set of two or more interacting or bound amino acid polymers.

The term "deep sequencing" refers to a method of sequencing a plurality of nucleic acids in parallel. See e.g., Bentley et al., *Nature* 2008, 456:53-59. In a typical deep sequencing protocol, nucleic acids (e.g. DNA fragments) are attached to the surface of a reaction platform (e.g., flow cell, microarray, and the like). The attached DNA molecules may be amplified in situ and used as templates for synthetic sequencing (i.e., sequencing by synthesis) using a detectable label (e.g. fluorescent reversible terminator deoxyribonucleotide). Representative reversible terminator deoxyribonucleotides may include 3'-O-azidomethyl-2'-deoxynucleoside triphosphates of adenine, cytosine, guanine and thymine, each labeled with a different recognizable and removable fluorophore, optionally attached via a linker. Where fluorescent tags are employed, after each cycle of incorporation, the identity of the inserted based may be determined by excitation (e.g., laser-induced excitation) of the fluorophores and imaging of the resulting immobilized growing duplex nucleic acid. The fluorophore, and optionally linker, may be removed by methods known in the art, thereby regenerating a 3' hydroxyl group ready for the next cycle of nucleotide addition.

I. Introduction

Provided herein, inter alia, are improved methods of sequencing native cellular nascent RNA transcripts. The methods of the invention exploit the stability of the RNA polymerase complex (e.g., the DNA-RNA-RNAP ternary complex) to capture nascent transcripts directly from live cells without crosslinking. The cellular nascent RNA transcripts can be converted into DNA using a library construction technique that allows sequencing to start at the 3' end. The identity and abundance of the 3' end of purified transcripts can then be revealed by deep sequencing with single nucleotide precision. Therefore, in some embodiments, the methods provide higher spatial resolution than other sequencing techniques and strategies. In addition, the methods may employ only active RNA polymerase and provide strand specific information.

II. Cellular Nascent RNA Transcript

Any cellular nascent RNA transcript can be detected and sequenced using the methods provided herein, e.g., a sense transcript, an antisense transcript, and an unstable transcript. A cellular nascent RNA transcript from any cell or any origin is contemplated to be within the scope of embodiments of the present invention. The cellular nascent RNA transcript can be from any appropriate cell including a prokaryotic cell or a eukaryotic cell. The cellular nascent RNA transcript can also be a viral RNA transcript derived from a cell infected with the virus. The cell may be any appropriate cell, include a bacterial cell or a eukaryotic cell and including, but not limited to, animal cells, fungal cells and plant cells.

A prokaryotic microorganism includes bacteria such as Gram positive, Gram negative and Gram variable bacteria and intracellular bacteria. Examples of bacteria contemplated herein include the species of the genera *Treponema, Borrelia, Neisseria, Legionella, Bordetella, Escherichia, Salmonella, Shigella, Klebsiella, Yersinia, Vibrio, Hemophilus, Rickettsia, Chlamydia, Mycoplasma, Staphylococcus, Streptococcus, Bacillus, Clostridium, Corynebacterium, Pseudomonas, Proprionibacterium, Mycobacterium, Ureaplasma* and *Listeria*. Particularly preferred species include *Escherichia coli, Treponema pallidum, Borrelia burgdorferi, Neisseria gonorrhea, Neisseria meningitidis, Legionella pneumophila, Bordetella pertussis, Salmonella typhi, Salmonella typhimurium, Shigella dysenteriae, Klebsiella pneumoniae, Yersinia pestis, Vibrio cholerae, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae, Listeria monocytogenes, Pseudomonas aeruginosa* and *Pseudomonas putida*.

A eukaryotic cell includes a yeast or fungus such as but not limited to *Microsporidium, Pneumocystis carinii, Candida albicans, Aspergillus, Histoplasma capsulatum, Blastomyces dermatitidis, Cryptococcus neoformans, Trichophyton* and *Microsporum*. The cells may also be from worms, insects, arachnids, nematodes, amoebae, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*. The eukaryotic cells may also be from mammals such as humans, primates, livestock animals, companion animals and laboratory test animals.

In some embodiments, the cell is a mammalian cell, such as a human cell or a cell from a domesticated animal (e.g. dog, cat, horse etc.) or a livestock animal (e.g., pig, cow etc.). In some embodiments, the cell forms part of an organ or an organism. The cell may also be obtained from an organism that is diseased to assess characteristics of a disease state. Thus, in some embodiments, the cell is or has been infected with a virus. In other embodiments, the cell is derived from an organism with a disease (e.g., diabetes, heart disease, Alzheimer's disease, etc.).

Viruses contemplated herein include HIV, hepatitis virus (e.g. Hep A, Hep B, Hep C and non-A, non-B Hep virus), adenoviruses, papovaviruses, herpes viruses: simplex, varicella-zoster, Epstein-Barr, CMV, pox viruses: smallpox, vaccinia, rhinoviruses, polio virus, rubella virus, arboviruses, rabies virus, foot and mouth disease virus, swine fever virus, Newcastle disease virus, respiratory viruses that cause the common cold, influenza viruses A and B, measles virus, mumps virus and HTLV I and II.

III. Arresting Transcription

The present invention provides a method of identifying a native cellular nascent RNA transcript. The method includes the step of arresting transcription in the cell. As defined herein, the term "arrest" refers to inhibition of transcription by at least 50% and preferably 80%, 90%, 95% or 100%. In some embodiments, the term "arrest" refers to inhibition of transcription initiation. In some embodiments, the term "arrest" refers to inhibition of transcription elongation. Accordingly, in some embodiments, arresting transcription refers to the slowing of transcription elongation by at least 50% in the given time period and preferably 80%, 90%, 95% or 100%. Methods of arresting transcription are well-known in the art. All of the above percentages are relative to cells not subject to transcription arresting procedures.

In some embodiments, the transcription of a cell is arrested by lowering the temperature of the cell. In some embodiments, the transcription of a cell is arrested by placing the cell on ice or under conditions to rapidly reduce the temperature to a level to inhibit or otherwise reduce transcription of the cell. In some embodiments, the transcription of a cell is arrested by lowering the temperature of the cell to, e.g., 10° C. or below, e.g., 5° C., 0° C., −10° C., −20° C., −40° C. In some embodiments, the transcription of a cell is arrested by contacting the cell with liquid nitrogen (e.g., forming a flash-frozen cell). The transcription of a cell can be easily arrested by contacting the cell with other alternative phase change materials of very low evaporating temperature type such as dry ice, liquid $CO_2$, or the like.

The transcription of a cell (e.g., the transcription elongation by RNA polymerase) can also be arrested by a transcription inhibitor, e.g., an RNA polymerase inhibitor. Examples of RNA polymerase inhibitors include, e.g., small molecules that inhibit RNA polymerase or interact with DNA to block transcription. Exemplary RNA polymerase inhibitors include actinomycin D, which intercalates into double stranded DNA and blocks the movement of RNA polymerase and rifampicin, an antibiotic which binds the β subunit of RNA polymerase and blocks initiation of transcription. Exemplary eukaryotic RNA polymerase inhibitors include the potent mushroom toxin α-amanitin, a cyclic octapeptide which binds to the polymerase with high affinity ($Kd=10^{-9}$ M). Exemplary antiviral RNA polymerase inhibitors include antiviral nucleoside analogs such as ribavirin, viramidine, 6-fluoro-3-hydroxy-2-pyrazinecarboxamide (T-705), 2'-deoxy-2'-fluoroguanosine, pyrazofurin, 3-deazaguanine, carbodine (see e.g. Shannon et al., Antimicrob Agents Chemother. (1981) 20:769-76), and cyclopenenyl cytosine (see e.g. Shigeta et al., Antimicrob Agents Chemother. (1988) 32:906-11).

Reversible or irreversible transcription inhibitors (e.g., RNA polymerase inhibitors) can be used. In some embodiments, an irreversible transcription inhibitor is used to arrest transcription of the cell.

Other methods of arresting transcription are well-known in the art. Preferably, the arresting of the transcription does not damage or modify the nascent RNA transcript, i.e., the nascent RNA transcript remains intact and native. Optionally, the step of arresting transcription in a cell can be omitted, e.g., the native cellular nascent RNA transcript can be purified directly from the cells of interest without the step of freezing the cells.

IV. Purifying a Cellular Nascent RNA Transcript

The cellular nascent RNA transcript can be purified using methods well-known in the art. In some embodiments, the cellular nascent RNA transcript is purified as part of an RNA polymerase complex. According to the present invention, the nascent RNA transcript need not be cross-linked to the RNA polymerase complex prior to the complex purification. Accordingly, in some embodiments, the nascent RNA transcript is not cross-linked to the RNA polymerase complex. Purification of the RNA polymerase complex can follow the standard protein purification procedure described below.

For example, an initial salt fractionation can separate many of the unwanted host cell proteins (or proteins derived from the cell culture media) from the RNA polymerase complex. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in a buffer and the excess salt removed if necessary, through either dialysis or diafiltration. Other methods that rely on solubility of proteins, such as cold ethanol precipitation, are well known to those of skill in the art and can be used to fractionate complex protein mixtures.

The RNA polymerase complex can also be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the RNA polymerase complex. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The RNA polymerase complex can also be separated from other proteins on the basis of their size, net surface charge, hydrophobicity, or affinity for ligands. In addition, antibodies raised against a segment of the RNA polymerase can be conjugated to column matrices and the RNA polymerase complex immunopurified. All of these methods are well known in the art.

Alternatively, the RNA polymerase complex can be purified using a recombinant tag. The cells of interest may be transformed with a recombinantly tagged RNA polymerase. The recombinant tags may then be used to purified the RNA polymerase complex. The tags can be affinity tags, epitope tags, fusion proteins tags, or a combination thereof. Whilst any purification tag may be employed, the following affinity tags, epitope tags, fusion proteins tags are preferred: His-tag (e.g., 6× histidine), preferably as a C-terminal and/or N-terminal tag; MBP (maltose binding protein)-tag; GST (glutathione-S-transferase)-tag; His-MBP-tag; GST-MBP-tag; Thioredoxin-tag; CBD (Chitin Binding Domain)-tag, HA-tag, FLAG-tag, and Myc-tag fusions. Eiptope tags may include, but are not limited to, Green Fluorescent Protein (GFP)-tag, GST (Glutathione-S-transferase)-tag, and the FLAG-tag.

It will be apparent to one of skill that chromatographic techniques can be performed at any scale and using equipment from many different manufacturers (e.g., Pharmacia Biotech).

DNA molecules can be removed from the RNA polymerase complex. In some embodiments, the RNA polymerase complex is contacted with a DNAase prior to, during, or after the purification procedure. Other methods of removing DNA molecules are well-known in the art.

Once the RNA polymerase complex is purified, the cellular nascent RNA transcript is separated from the RNA polymerase complex. For example, the cellular nascent RNA transcript is separated from one or more RNA polymerase complex proteins, e.g., the RNA polymerase. Methods of separating the cellular nascent RNA transcript from the RNA polymerase complex is well-known in the art.

In some embodiments, the separated cellular nascent RNA transcript can be further purified. Purification of the cellular nascent RNA transcript can be made in accordance with a conventional method, for example, the mRNA can be purified by adsorption and elution using an oligo(dT)-cellulose column. The mRNA can be further fractionated by, for example, a sucrose density gradient centrifugation, if necessary. Alternatively, commercially available extracted and purified mRNA can be used.

V. Sequencing a Cellular Nascent RNA Transcript

The cellular nascent RNA transcript can be sequenced using tools and method well-known to those of skill in the art. For example, a direct sequencing technique may be employed (e.g., Sanger sequencing). In some embodiments, a deep sequencing technique is used. Certain embodiments employ sequencing platforms of Illumina, Inc. (San Diego, Calif.) and/or 454 Corporation (Roche Diagnostics, Basel, Switzerland), e.g., the Genome Sequencer FLX System, which employs pyrosequencing to provide long read lengths and very high single-read accuracy. In some embodiments, other sequencing platforms are utilized, including, but not limited to OmniMoRA (Reveo, Inc. (Elmsford, N.Y.)), VisiGen® (VisiGen Biotechnologies, Inc. (Houston, Tex.)), SBS technology (Intelligent Bio-Systems (Waltham, Mass.)), or Hybridization-Assisted Nanopore Sequencing (HANS; NABsys Inc. (Providence, R.I.)), or the target fragment isolated may be sent to a third party for further analysis and/or sequencing (e.g., Really Tiny Stuff, Inc. (Cohasset, Mass.)). In general, the invention is not limited to any particular methodology or product for analyzing the cellular nascent RNA transcript.

In some embodiments, the sequencing includes immobilizing the nucleic acid (e.g., the cellular nascent RNA transcript) on a flow cell surface. In some embodiments the nucleic acid is immobilized on a flow cell or microarray and subjected to the procedures described herein or known in the art for sequencing. Bridge amplification may occur within a flow cell having immobilized nucleic acids thereon, or within a microarray. In some embodiments, the microarray includes a plurality of assay wells having a population of microbeads randomly distributed thereon. In some embodiments, the nucleic acid (e.g., the cellular nascent RNA transcript) is immobilized on the microbeads, which in turn are affixed to the microarray.

In some embodiments, the sequencing is accomplished using a sequencing-by-synthesis technique. The term "sequencing by synthesis" refers to the sequencing of a nucleic acid sequence by synthesis of the complementary strand, as known in the art and described herein. The sequence by synthesis technique may be selected from the group consisting of pyrosequencing, sequencing by ligation and sequencing by extension. The term "pyrosequencing," as known in the art, refers to a method of sequencing by synthesis which relies on detection of pyrophosphate release on nucleotide incorporation. See e.g., Ronaghi et al., *Science* 1998, 281:363; Ronaghi et al., *Anal. Biochem.* 242:84; Nyren et al., *Methods Mol. Biology.*, 2007, 373:1-14. The term "sequencing by ligation" refers to a DNA sequencing method that uses DNA ligase, as known in the art, to identify the nucleotide present at a given position in a DNA sequence. The term "sequencing by extension" refers to a DNA sequencing method wherein a primer is extended with a known or detectable nucleotide, as known in the art.

As described herein, the present methods can be used in conjunction with a variety of sequencing techniques. In some embodiments, the process to determine the nucleotide sequence (e.g., the cellular nascent RNA transcript) can be an automated process.

Templates (e.g., the cellular nascent RNA transcript) may be amplified on beads, for example using emulsion PCR methods. In order to use emulsion based amplification techniques with a single template per emulsion bubble, a single primer is attached to the bead, and a single primer is in solution, thereby amplifying the templates such that one end of the duplex is attached to the bead. The hybridized strand can be removed by denaturing the duplex, thereby leaving the immobilized single strand on the bead. The single stranded templates can be captured onto a surface via primers complementary to the templates. Exemplary emulsion-based amplification techniques that can be used in a method of the invention are described in US 2005/0042648; US 2005/0079510; US 2005/0130173 and WO 05/010145, each of which is incorporated herein by reference in its entirety and for all purposes.

Templates (e.g., the cellular nascent RNA transcript) can be amplified on a surface using bridge amplification to form nucleic acid clusters. Bridge amplification gives a double stranded template where both ends are immobilized. Methods of generating nucleic acid clusters for use in high-throughput nucleic acid technologies have been described, as noted above. See, for example, U.S. Pat. No. 7,115,400, U.S. Patent Application Publication Nos. 2005/0100900 and 2005/0059048, and PCT Publication Nos. WO 98/44151, WO 00/18957, WO 02/46456, WO 06/064199, and WO 07/010,251, each of which is incorporated by reference herein in its entirety and for all purposes.

Some embodiments include sequencing by synthesis (SBS) techniques. SBS techniques generally involve the enzymatic extension of a nascent nucleic acid strand (e.g., the cellular nascent RNA transcript) through the iterative addition of nucleotides or oligonucleotides against a template strand. In traditional methods of SBS, a single nucleotide monomer may be provided to a target nucleotide in the presence of a polymerase in each delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other. For example, the different nucleotides present in a sequencing reagent can have different labels and they can be distinguished using appropriate optics as exemplified by the sequencing methods developed by Solexa (now Illumina, Inc.).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1):84-9; Ronaghi, M. (2001) "Pyrosequencing sheds light on DNA sequencing." *Genome Res.* 11(1):3-11; Ronaghi, M., Uhlen, M. and Nyren, P. (1998) "A sequencing method based on real-time pyrophosphate." *Science* 281(5375):363; U.S. Pat. No. 6,210,891; U.S. Pat. No. 6,258,568 and U.S. Pat. No. 6,274,320, the disclosures of which are incorporated herein by reference in their entireties and for all purposes). In pyrosequencing, released PPi can be detected by being immediately converted to adenosine triphosphate (ATP) by ATP sulfurylase, and the level of ATP generated is detected via luciferase-produced photons.

In another type of SBS, cycle sequencing is accomplished by stepwise addition of reversible terminator nucleotides containing, for example, a cleavable or photobleachable dye label as described, for example, in U.S. Pat. No. 7,427,67, U.S. Pat. No. 7,414,163 and U.S. Pat. No. 7,057,026, the disclosures of which are incorporated herein by reference and for all purposes. This approach is being commercialized by Solexa (now Illumina Inc.), and is also described in WO 91/06678 and WO 07/123,744 (filed in the United States patent and trademark Office as U.S. Ser. No. 12/295,337), each of which is incorporated herein by reference in their entireties and for all purposes. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In particular embodiments some or all of the nucleotide monomers can include reversible terminators. In such embodiments, reversible terminators/cleavable fluors can include fluor linked to the ribose moiety via a 3' ester linkage (Metzker, *Genome Res.* 15:1767-1776 (2005), which is incorporated herein by reference and for all purposes). Other approaches have separated the terminator chemistry from the cleavage of the fluorescence label (Ruparel et al., *Proc Natl Acad Sci USA* 102: 5932-7 (2005), which is incorporated herein by reference in its entirety and for all purposes). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties and for all purposes.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010,251, the disclosures of which are incorporated herein by reference in their entireties and for all purposes.

Some embodiments can utilize sequencing by ligation techniques. Such techniques utilize DNA ligase to incorporate nucleotides and identify the incorporation of such nucleotides. Example ligation-based systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties and for all purposes.

Some embodiments can utilize nanopore sequencing (Deamer, D. W. & Akeson, M. "Nanopores and nucleic acids: prospects for ultrarapid sequencing." *Trends Biotechnol.* 18:147-151 (2000); Deamer, D. and D. Branton, "Characterization of nucleic acids by nanopore analysis". *Acc. Chem. Res.* 35:817-825 (2002); Li, J., M. Gershow, D. Stein, E. Brandin, and J. A. Golovchenko, "DNA molecules and configurations in a solid-state nanopore microscope" *Nat. Mater.* 2:611-615 (2003), the disclosures of which are incorporated herein by reference in their entireties and for all purposes). In such embodiments, the target nucleic acid or nucleotides released from the target nucleic acid pass through a nanopore. The nanopore can be a synthetic pore or biological membrane protein, such as α-hemolysin. As the target nucleic acid or nucleotides pass through the nanopore, each base-pair (or base) can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53:1996-2001 (2007); Healy, K. "Nanopore-based single-molecule DNA analysis." *Nanomed.* 2:459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130:818-820 (2008), the disclosures of which are incorporated herein by reference in their entireties and for all purposes).

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211,414 (each of which is incorporated herein by reference in their entireties and for all purposes) or nucleotide incorporations can be detected with zero-mode waveguides as described, for example, in U.S. Pat. No. 7,315,019 (which is incorporated herein by reference in its entirety and for all purposes) and using fluorescent nucleotide analogs and engineered polymerases as described, for example, in U.S. Pat. No. 7,405,281 and U.S. Patent Application Publication No. 2008/0108082 (each of which is incorporated herein by reference in their entireties and for all purposes). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299:682-686 (2003); Lundquist, P. M. et al. "Parallel confocal detection of single molecules in real time." *Opt. Lett.* 33:1026-1028 (2008); Korlach, J. et al. "Selective aluminum passivation for targeted immobilization of single DNA polymerase molecules in zero-mode waveguide nanostructures." *Proc. Natl. Acad. Sci. USA* 105:1176-1181 (2008), the disclosures of which are incorporated herein by reference in their entireties and for all purposes). In one example single molecule, real-time (SMRT) DNA sequencing technology provided by Pacific Biosciences Inc. can be utilized with the methods described herein. In some embodiments, a SMRT chip or the like may be utilized (U.S. Pat. Nos. 7,181,122, 7,302,146, 7,313,308, incorporated by reference in their entireties and for all purposes). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about $1 \times 10-21$ L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J. et al., "Long, processive enzymatic DNA synthesis using 100% dye-labeled terminal phosphate-linked nucleotides." *Nucleosides, Nucleotides and Nucleic Acids,* 27:1072-1083, 2008; incorporated by reference in its entirety and for all purposes). The label is cleaved from the nucleotide monomer on incorporation of the nucleotide into the polynucleotide. Accordingly, the label is not incorporated into the polynucleotide, increasing the signal:background ratio. Moreover, the need for conditions to cleave a label from a labeled nucleotide monomers is reduced.

An additional example of a sequencing platform that may be used in association with some of the embodiments described herein is provided by Helicos Biosciences Corp. In some embodiments, TRUE SINGLE MOLECULE SEQUENCING (tSMS)™ can be utilized (Harris T. D. et al., "Single Molecule DNA Sequencing of a viral Genome" *Science* 320:106-109 (2008), incorporated by reference in its entirety and for all purposes). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomer, namely, A, C, G, or T, are delivered one at a time to the target nucleic acid in the presence of DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

An additional example of a sequencing platform that can be used in association with the methods described herein is provided by Complete Genomics Inc. Libraries of target nucleic acids (e.g., the cellular nascent RNA transcripts) can be prepared where target nucleic acid sequences are interspersed approximately every 20 bp with adaptor sequences. The target nucleic acids can be amplified using rolling circle replication, and the amplified target nucleic acids can be used to prepare an array of target nucleic acids. Methods of sequencing such arrays include sequencing by ligation, in particular, sequencing by combinatorial probe-anchor ligation (cPAL).

In some embodiments using cPAL, about 10 contiguous bases adjacent to an adaptor may be determined. A pool of probes that includes four distinct labels for each base (A, C, T, G) is used to read the positions adjacent to each adaptor. A separate pool is used to read each position. A pool of probes and an anchor specific to a particular adaptor is delivered to the target nucleic acid in the presence of ligase. The anchor hybridizes to the adaptor, and a probe hybridizes to the target nucleic acid adjacent to the adaptor. The anchor and probe are ligated to one another. The hybridization is detected and the anchor-probe complex is removed. A different anchor and pool of probes is delivered to the target nucleic acid in the presence of ligase.

The sequencing methods described herein can be advantageously carried out in multiplex formats such that multiple different target nucleic acids (e.g., the cellular nascent RNA transcripts) are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

In some embodiments, the sequencing further includes bridge amplification. The term "bridge amplification" refers to a solid phase replication method in which primers are bound to a solid phase, e.g., flow cell, microarray, and the like. The term "bridge" in this context refers to the fact that during the annealing step, the extension product from one bound primer forms a bridge to the other bound primer. All amplified products are covalently bound to the surface, and can be detected and quantified without electrophoresis. Sequencing by synthesis methods may be employed with any appropriate amplification method, including for example PCR. In some embodiments, the sequencing is accomplished using deep sequencing, Methods for amplification of nucleic acids are well known in the art. Any appropriate method of amplification may be used in conjunction with the methods disclosed herein. For example, a useful amplification technique is PCR (polymerase chain reaction). Methods of PCR include basic PCR (Saiki et al., Science 1985, 230:1350-1354), real-time PCR (RT-PCR) (Nanashima et al., *J. Biol. Chem.* 2008, 283: 16868-16875), hot-start PCR (Carothers et al., *Biotechniques* 1989, 7:494-9 1989; Krishnan et al. *Nucl. Acids Res.* 1991, 19:1153; Clark, *Nucl. Acids Res.* 1988, 16:9677-86; Lin & Jayasena, *J. Mol. Biol.* 1997, 271:100-11; Dang & Jayasena, *J. Mol. Biol.* 1996, 264:268-78; Scalice et al. *J. Immunol. Methods,* 1994, 172:147-63; Sharkey et al., *Biotechnology* 1994, 12:506-9; Moretti, T. et al., *BioTechniques* 1998, 25:716-22), long PCR (Barnes, *Proc. Natl. Acad. Sci. USA* 1994, 91:2216-20), quantitative endpoint PCR (Gaudette & Crain, *Nucl. Acids Res.* 1991, 19:1879-84; Murphy et al., *Biochemistry* 1990, 29:10351-10356), quantitative real-time PCR (Lee et al., *Nucl. Acids Res.* 1993, 21:3761-3766; Bernard et al., *Anal. Biochem.* 1998, 255:101-107; Sherrill et al., *J. Am. Chem. Soc.* 2004, 126:4550-4556; Frackman et al., *Promega Notes* 2006, 92:10-13); rapid amplified polymorphic DNA analysis (McClelland & Welsh, *PCR Methods Appl.* 1994, 4:S59-65; Power, *J. Hosp. Infect.* 1996, 34:247-265; Black, 1993), rapid amplification of cDNA ends (Troutt et al., *Proc. Natl. Acad. Sci. USA* 1992, 89:9823-9825; Edwards et al., *Methods in Molecular Biology* (Vol. 15), White, B. A., ed., Humana Press, Totowa, N.J., 1991; Liu & Gorovsky, *Nucl. Acids Res.* 1993, 21:4954-60; Fromont-Racine et al., *Nucl. Acids Res.* 1993, 21:1683-1684), differential display PCR (Liang & Pardee, *Science* 1992, 257:967-71), in situ PCR (Haase et al., *Proc. Natl. Acad. Sci. USA* 1990, 87:4971-4975), and high fidelity PCR (Cline et al., *Nucl. Acids Res.* 1996, 24:3546-3551).

As described herein, nucleic acid molecules (e.g., the cellular nascent RNA transcript) can be amplified on beads, for example using emulsion PCR methods. Exemplary emulsion-based amplification techniques that can be used in a method disclosed herein are described in US 2005/0042648; US 2005/0079510; US 2005/0130173 and WO 05/010145, each of which is incorporated herein by reference in its entirety and for all purposes. As further described herein, nucleic acid molecules can be amplified on a surface using bridge amplification to form nucleic acid clusters. Exemplary methods of generating nucleic acid clusters for use in high-throughput nucleic acid technologies have been described. See, for example, U.S. Pat. No. 7,115,400, U.S. Patent Application Publication Nos. 2005/0100900 and 2005/0059048, and PCT Publication Nos. WO 98/44151, WO 00/18957, WO 02/46456, WO 06/064199, and WO 07/010,251, each of which is incorporated by reference herein in its entirety and for all purposes.

VI. Applications

The methods of the invention can be used in various applications. For example, the methods of the invention can be used in assessing transcriptional activity in a cell. In some embodiments, the methods of the invention are used in assessing transcriptional activity in a cell in response to a stimulus, e.g., an external or internal stimulus, prior to the arresting of the transcription. In some embodiments, the methods of the invention are used in assessing transcriptional activity in cells in different developmental states or stages.

In some embodiments, the transcriptional activity of cells in response to a stimulus can be assessed. In some embodiments, the transcriptional activity of the cells in the presence or absence of the stimulus are assessed and compared. As defined herein, the term "stimulus" refers to a changeable parameter surrounding the cell, e.g., the temperature, the pH, the effects of small molecules, the effects of inhibitory nucleic acids such as co-suppression molecules, antisense molecules, RNAi-inducing molecules, as well as the effects of protein molecules.

In some embodiments, the stimulus is a small molecule (e.g., a small molecule drug). Transcriptional activity may be determined in the presence or absence of introduced small molecules. Examples of suitable small molecules suitable for the methods of the invention include chemicals from a chemical library or molecules identified from natural product screening.

In some embodiments, the stimulus is an inhibitory nucleic acid. Transcriptional activity may be determined in the presence or absence of introduced inhibitory nucleic acids. Inhibitory nucleic acids suitable for the methods of the invention include genetic molecules such as co-suppression or antisense molecules or RNAi-inducing molecules (e.g., siRNA, shRNA, ribozymes). In some embodiments, antisense molecules or RNAi-inducing molecules are from about 10 base pairs long to about 2000 base pairs long, or from about 12 to about 30 base pairs long such as 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, base pairs in length. In some embodiments, the antisense molecule or RNAi-inducing molecule is about 10, 20, 30, 40, 50, 60, 70, 80, 90 or 100 base pairs in length. In some embodiments, the antisense molecule or RNAi-inducing molecule is about 100, 200, 300, 400, 500, 600, 700, 800, 900 or 1000 base pairs in length. In some embodiments, the antisense molecule or RNAi-inducing molecule (e.g. antisense strand) is about 13, 18, or 22 base pairs in length. In some embodiments, co-suppression molecules include double-stranded RNA molecules forming a hairpin with or without single-stranded portions in the form of a "bulge" or "bubble" Inhibitory nucleic acids can be delivered to a cell by direct transfection (e.g., using liposomal transfection reagents) or transfection and expression via an expression vector (e.g., a mammalian expression vector or a viral expression vector).

In some embodiments, the stimulus is a protein molecule. Transcriptional activity may be determined in the presence or absence of introduced protein molecules. Examples of protein molecules suitable for the methods of the invention include DNA/RNA-binding proteins, antibodies, therapeutic proteins, protein hormones, transcription factors for inducing pluripotent stem cells, and various enzymes. In some embodiments, the protein molecules are co-expressed in the cell. In some embodiments, the protein molecules are exogenously introduced in the cell. In some embodiments, the protein molecules are linked to a polypeptide that enhances the ability of the protein molecules (e.g. transcription factor) to enter the cell (e.g., linked as a fusion protein or otherwise covalently or non-covalently linked). Examples of polypeptide sequences that enhance transport across membranes include, but are not limited to, the *Drosophila* homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55: 1 289-1193, 1988); Kaposi FGF signal sequence (kFGF); protein transduction domain-4 (PTD4); Penetratin, M918, Transportan-10; a nuclear localization sequence, a PEP-I peptide; an amphipathic peptide (e.g., an MPG peptide); delivery enhancing transporters such as described in U.S. Pat. No. 6,730,293; and commercially available Penetratin™ 1 peptide, and the Diatos Peptide Vectors ("DPVs") of the Vectocell® platform available from Daitos S.A. of Paris, France. See also, WO/2005/084158 and WO/2007/123667 and additional transporters described therein. A number of polypeptides capable of mediating introduction of associated molecules into a cell have been described previously and can be adapted to the present invention. See, e.g., Langel (2002) Cell Penetrating Peptides CRC Press, Pharmacology and Toxicology Series.

In some embodiments, the molecules suitable for the methods of the invention include molecules from a "combinatorial chemical library." A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487-493, Houghton et al. (1991) *Nature,* 354:84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random biooligomers (PCT Publication WO 92/00091, 9 Jan. 1992), benzodiazepines (U.S. Pat. No. 5,288,514), diversomets such as hydantoins, benzodiazepines and dipeptides (Hobbs et al., (1993) *Proc. Nat. Acad. Sci. USA* 90:69096913), vinylogous polypeptides (F3agihara. et al. (1992) *J. Amer. Chem. Soc.* 114:6568), nonpeptidal peptidomimetics with a Beta D Glucose scaffolding (Hirschmann et al., (1992) *J. Amer. Chem. Soc.* 114: 92179218), analogous organic syntheses of small compound libraries (Chen et al. (1994) *J. Amer. Chem. Soc.* 116:2661), oligocarbamates (Cho, et al., (1993) *Science* 261:1303), and/or peptidyl phosphonates (Campbell et al., (1994) *J. Org. Chem.* 59:658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96110287), carbohydrate libraries (see, e.g., Liang et al. (1996) *Science,* 274:1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines 5,288, 514, and the like).

Devices for the preparation of combinatorial libraries are commercially available (see, eg., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Furthermore, the transcriptional activity of cells at various points in their development may also be assessed. For example, in some embodiments, the transcriptional activity of undifferentiated stem cells to differentiated stem cells or committed lineage cells are assessed and compared. In some embodiments, the transcriptional activity of diseased cells (e.g., cells derived from an organism with a disease or cells infected with a virus) and normal cells are assessed and compared.

Accordingly, another aspect of the present invention provides a method for determining changes in transcriptional activity in a cell or cell linage. The method involves identifying cellular nascent RNA transcripts in cells in the presence or absence of a stimulus, or cells at different developmental stages, or diseased cells and normal cells. The method further involves arresting transcription in the cells described above, and purifying the native cellular nascent RNA transcripts from these cells (e.g., as part of an RNA polymerase complex). According to the methods of the invention, these native cellular nascent RNA transcripts are then sequenced. Based on the sequences of the native cellular nascent RNA transcripts, the transcriptional activity in these cells are assessed and compared. For example, the changes in transcriptional activity in cells in the presence or absence of a stimulus are measured and compared. The differences in transcriptional activity in cells at different developmental stages are detected and compared. Further the transcriptional activity in normal cells and diseased cells can also be compared.

The methods of the invention disclosed herein can be used for various assays. For examples, the methods described herein can be used to detect relative or absolute gene expression levels as indicated by cellular nascent RNA transcripts, or detect the relative or absolute amount of noncoding RNAs or unstable RNAs. In some embodiments, the methods described herein can be used to detect allelic expressions. In some embodiments, the methods described herein can be used for haplotype assays and phasing of multiple SNPs within chromosomes. In some embodiments, the methods described herein can be used to detect DNA methylation state, mRNA alternate splicing and level of splice variants. Further, the methods can be used to identify or detect the presence of microbe or viral content in food and environmental samples, or identify pathologies in plants, human, microbes, and animals. The methods of the invention can also be used in medical diagnosis.

EXAMPLES

The following examples are offered to illustrate, but not to limit the claimed invention.

Example 1

Nascent Transcript Sequencing Visualizes Transcription at Nucleotide Resolution

Transcription is more complicated than what was thought even a few years ago both in the intricate use of post-initiation control and the mass production of rapidly degraded transcripts. Dissection of these pathways requires strategies for precisely following transcripts as they are being produced. Here we present an approach (native elongating transcript sequencing, NET-seq), based on deep sequencing of 3' ends of nascent transcripts associated with RNA polymerase, to monitor transcription at nucleotide resolution. Application of NET-seq in Saccharomyces cerevisiae reveals that while promoters are generally capable of divergent transcription, the Rpd3S deacetylation complex enforces strong directionality to most promoters by suppressing antisense transcript initiation. Our studies also reveal pervasive polymerase pausing and backtracking throughout the body of transcripts. Average pause density shows prominent peaks at each of the first four nucleosomes, with the peak location occurring in good agreement with in vitro biophysical measurements. Thus nucleosome-induced pausing represents a major barrier to transcriptional elongation in vivo.

To monitor the transcriptional states of unperturbed cells, we sought to determine the precise in vivo position of all active RNAP complexes. Here we present an approach (native elongating transcript sequencing, NET-seq) that accomplishes this goal by exploiting the extraordinary stability of the DNA-RNA-RNAP ternary complex (Cai, H. & Luse, D. S., J. Biol. Chem. 262:298-304 (1987)) to capture nascent transcripts directly from live cells without crosslinking. The identity and abundance of the 3' end of purified transcripts are revealed by deep sequencing (Bentley, D. R. et al., Nature 456:53-59 (2008)) thus providing a quantitative measure of RNAP density with single nucleotide precision. Using NET-seq, we expose rapidly degraded transcription products, locate the position of RNAP pauses, and identify factors and chromatin structure that regulate these transcription events.

Quantitative Description of Transcription Activity at Nucleotide Resolution

Figure 7:
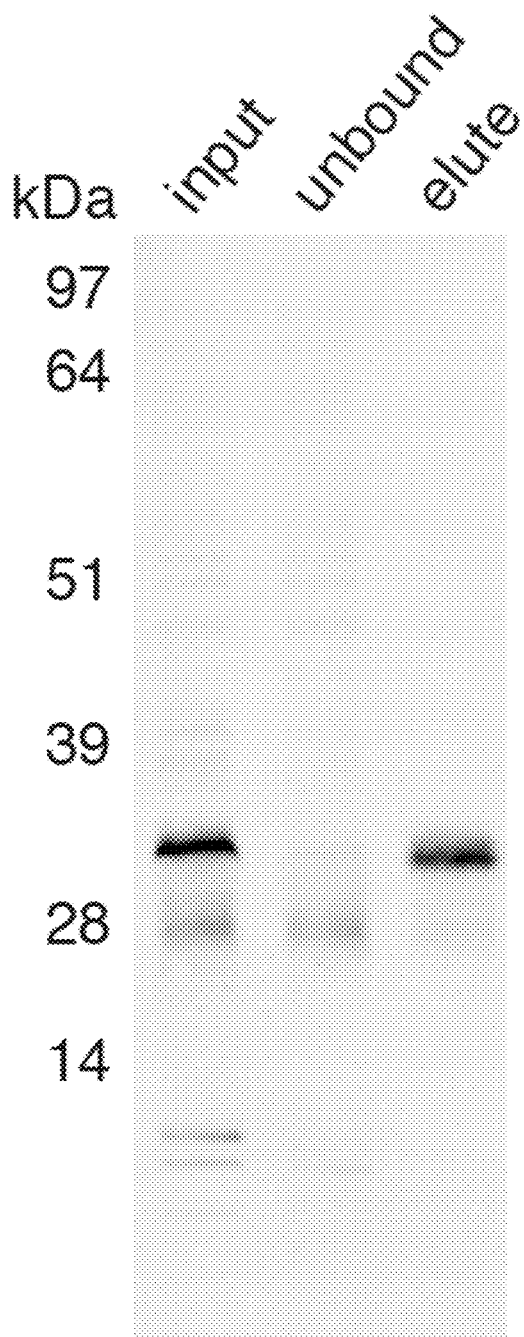
FIG. 7 Western blot detecting FLAG-labeled Rpb3 of immunoprecipitation samples of input lysate, unbound lysate and eluted protein.

We focused on the transcription by RNAPII of protein-coding genes in the budding yeast Saccharomyces cerevisiae, although the NET-seq approach should readily adaptable to other systems. To facilitate purification, we worked with a strain that endogenously expressed a functional variant of RNAPII with a 3×-FLAG epitope attached to its third subunit (Rpb3). Log-phase cultures were collected by filtration and flash frozen in liquid nitrogen (FIG. 1a). After cryogenic lysis, RNAPII was efficiently immunoprecipitated (FIG. 7). We prepared the co-purified RNA for deep sequencing using a protocol that allows efficient RNA capture while minimizing bias (Ingolia, N. T. et al., Science 324:218-223 (2009)) and sequenced 40 bases from the 3' end. The alignment of these sequences to the yeast genome identified the final nucleotide that was incorporated by RNAPII, and the number of sequencing reads at each position along the genome indicated the density of transcriptionally active RNA polymerases at that site (FIG. 1b, alignment statistics displayed in Table 1). A metagene analysis of RNAPII distribution across transcription units shows higher RNAPII density for the first 700 bp from the 5' end (FIG. 1c) consistent with lower resolution observations seen using a global run-on approach (Rodriguez-Gil, A. et al., Nucleic Acids Research (2010)).

Figure 1B:
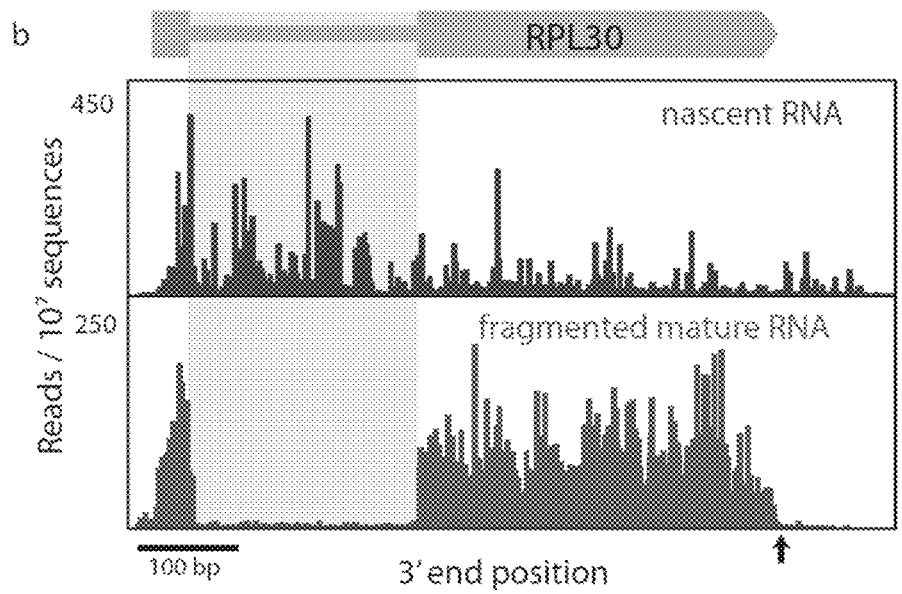
Figure 1C:
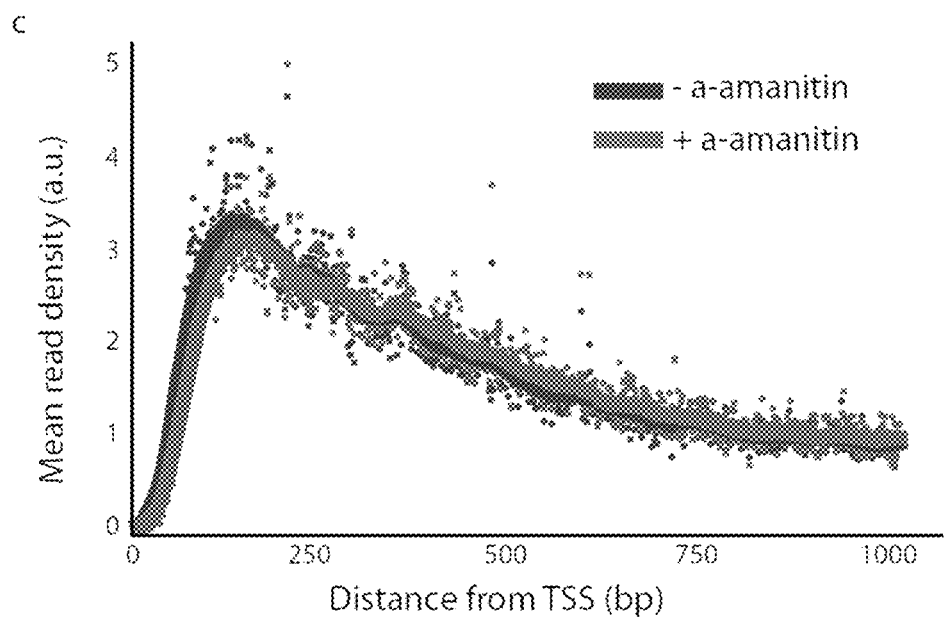

Several observations argue that we are detecting nascent transcription. First, we robustly capture transcripts from introns and regions after polyadenylation sites; areas which are present in nascent transcripts but absent from mature messages (FIG. 1b). Second, we verified that transcripts do not associate with RNAPII after cell lysis (Table 2). Third, we saw negligible degradation of RNA under the IP conditions. Nevertheless, our library generation protocols prevent detection of co-purified degradation products by requiring that input RNAs have 3' hydroxyl termini as hydrolysis and degradation products primarily have terminal phosphates (Markham, R. & Smith, J. D., Biochem. J. 52:552-557 (1952)). Lastly, we saw that transcription did not proceed during processing of lysates since addition of the transcription inhibitor, α-amanitin, to the IP did not change the RNAPII density (FIG. 1c).

Figure 8D:
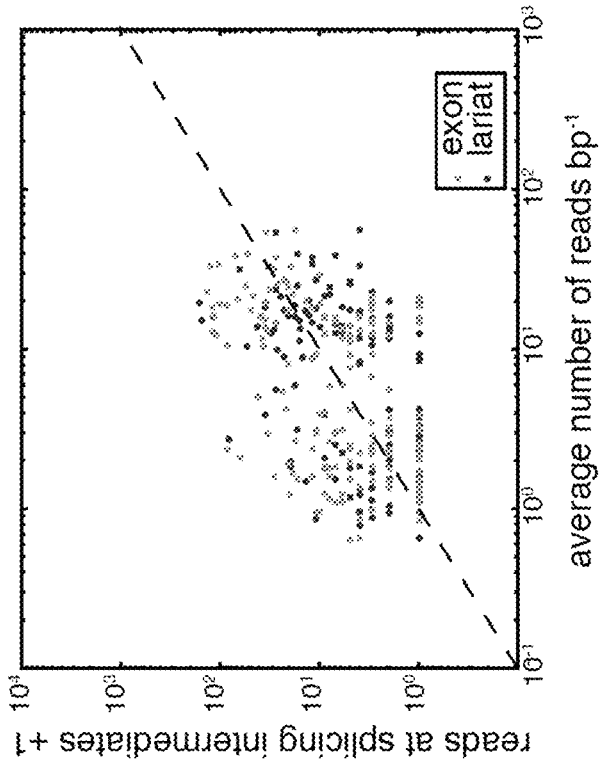
Figure 8C:
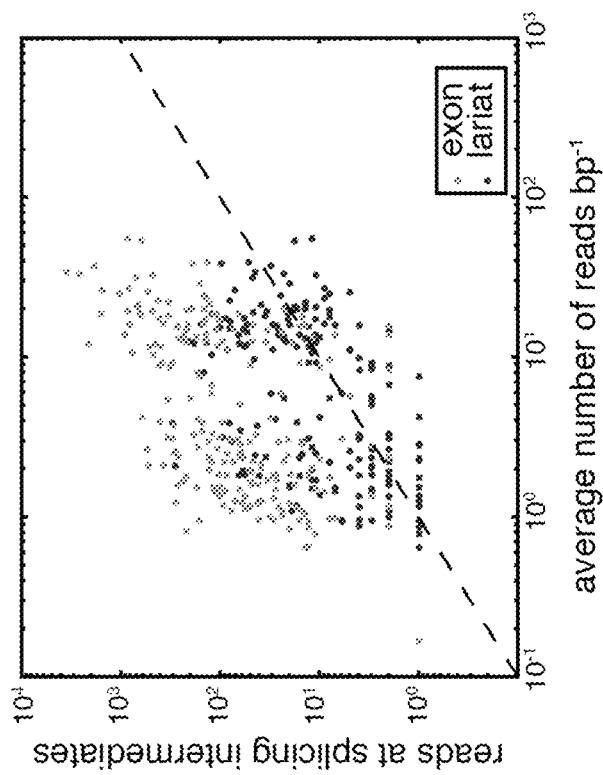

In addition to nascent transcripts, the RNAPII IP captures splicing intermediates (i.e. the 5' exon and the excised lariat). Their 3' hydroxyl termini allow them to appear in our data at the 3' ends of exons and introns (FIGS. 8 and 11). These observations suggest the widespread existence of co-transcriptional splicing in yeast and establish NET-seq as a powerful tool for studying such events.

Direct Observation of Transcription of Rapidly Degraded RNA

NET-seq monitors transcripts regardless of their stability, making it ideally suited to the analysis of unstable transcripts. Recent studies have revealed a class of cryptic unstable transcripts (CUTs) that are short (less than ~700 nucleotides), upstream and antisense to an annotated gene and rapidly degraded by the exosome (2-4; 15; 21). Divergent transcription, yielding the production of antisense CUTs and mature messages from the sense direction, is seen at many promoters in both yeast and metazoans. The observation of widespread divergent transcription was surprising and it remains unclear how antisense transcripts initiate and what biological function they may have. It is likely that the nucleosome-free region (NFR) associated with promoters facilitates antisense transcription. Additionally, it has been suggested that antisense and sense transcription levels are codependent (Core, L. J. et al., *Science* 322:1845-1848 (2008); Seila, A. C. et al., *Science* 322:1849-1851 (2008)) as transcription in the sense direction could promote upstream antisense transcription (and vice versa) by creating negatively supercoiled DNA and recruiting factors that set permissive histone marks (Seila, A. C. et al., *Cell Cycle* 8:2557-2564 (2009)). Critical evaluation of these hypotheses has been limited by the difficulty in quantitatively monitoring the levels of unstable antisense transcripts.

As NET-seq directly monitors the production of transcripts, we were able to quantify the relative amounts of nascent sense and antisense transcripts (FIG. 2a, b). We focused our analysis on promoters between genes encoded on the same strand (tandem genes), because in those instances, antisense transcripts can be clearly differentiated from the stable upstream transcript. To quantitate divergent transcription, we integrated the transcript levels for the first 500 bp of transcribed DNA in each direction. While we clearly observed divergent promoters, the large majority of promoters had much less antisense transcription than sense transcription; for more than half the promoters, sense transcription was at least eight times higher than antisense transcription and for 80% of the promoters the sense-to-antisense transcription ratio exceeded three-fold (FIG. 2b). Notably, a comparison between the levels of sense and antisense transcription showed only modest correlation (Spearman correlation coefficient, $r_s$=0.34) (FIG. 2c).

Figure 9A:
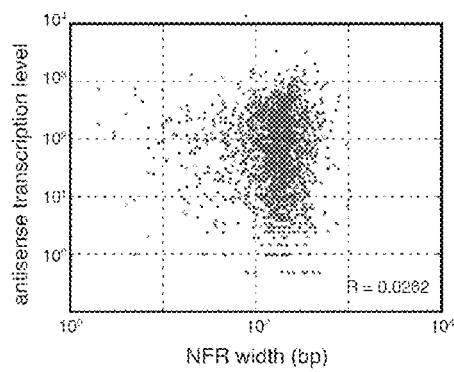
FIG. 9A-9D: Antisense transcription correlations.
Figure 9B:
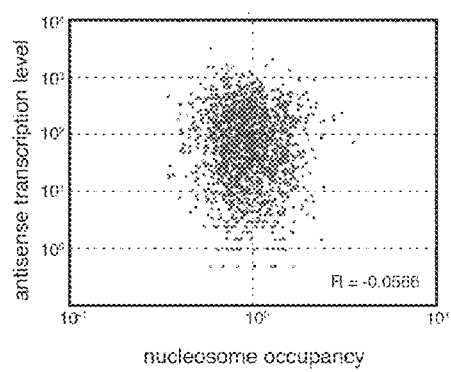
Figure 9C:
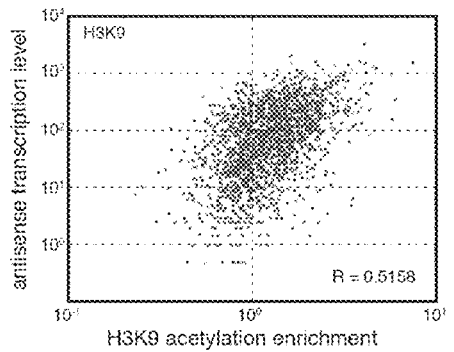
Figure 9D:
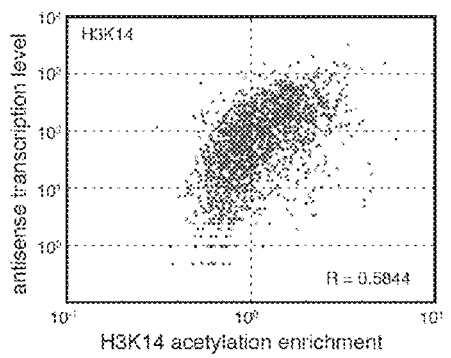
Figure 11A:
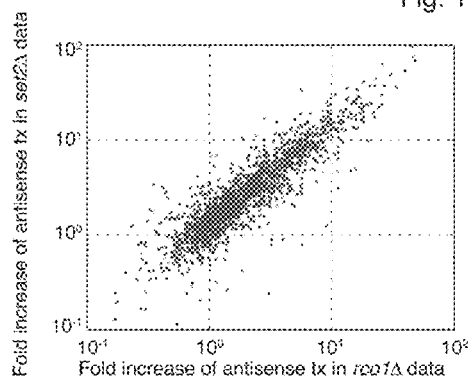
FIG. 11A-11D: Comparison of fold increases of antisense transcription (tx) in mutant strains compared to that in wild type.
Figure 11B:
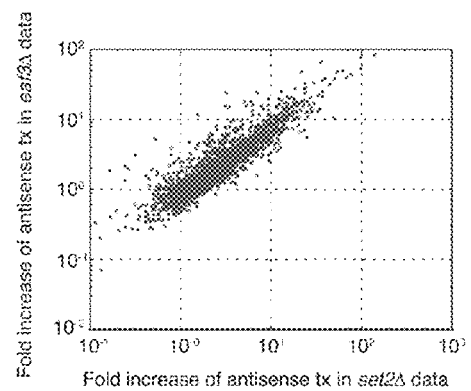
Figure 11C:
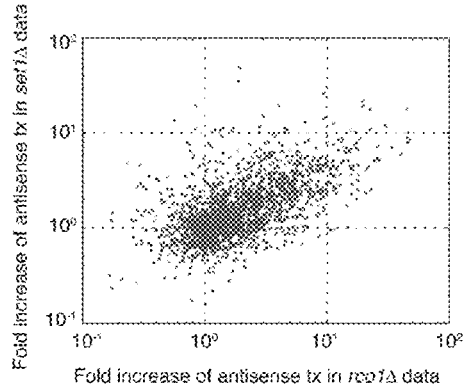
Figure 11D:
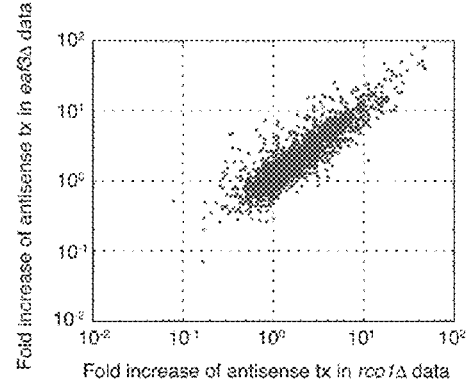

The above analysis establishes that antisense transcription is not an obligatory consequence of having an active promoter. What then dictates whether a promoter is directional? Transcription initiation is known to occur in NFRs, however, we failed to see a correlation when we compared antisense transcription levels with published data (Weiner, A. et al., *Genome Res* 20:90-100 (2010)) reporting on promoter NFR size and promoter average nucleosome occupancy (FIG. 9a-b). We also investigated whether histone modifications associated with active promoters correlated with antisense transcription since it was observed that H3 acetylation peaks in regions of antisense transcription in human fibroblasts (Core, L. J. et al., *Science* 322:1845-1848 (2008)). Remarkably, we found a strong positive correlation ($r_s$=0.65) between antisense transcription levels and earlier measurements of the levels of H4 (and to a lesser extent H3) acetylation enrichment (Pokholok, D. K. et al., *Cell* 122:517-527 (2005)) (FIG. 2d and FIG. 9c-d).

Rpd3S Promotes Promoter Directionality

Figure 3A:
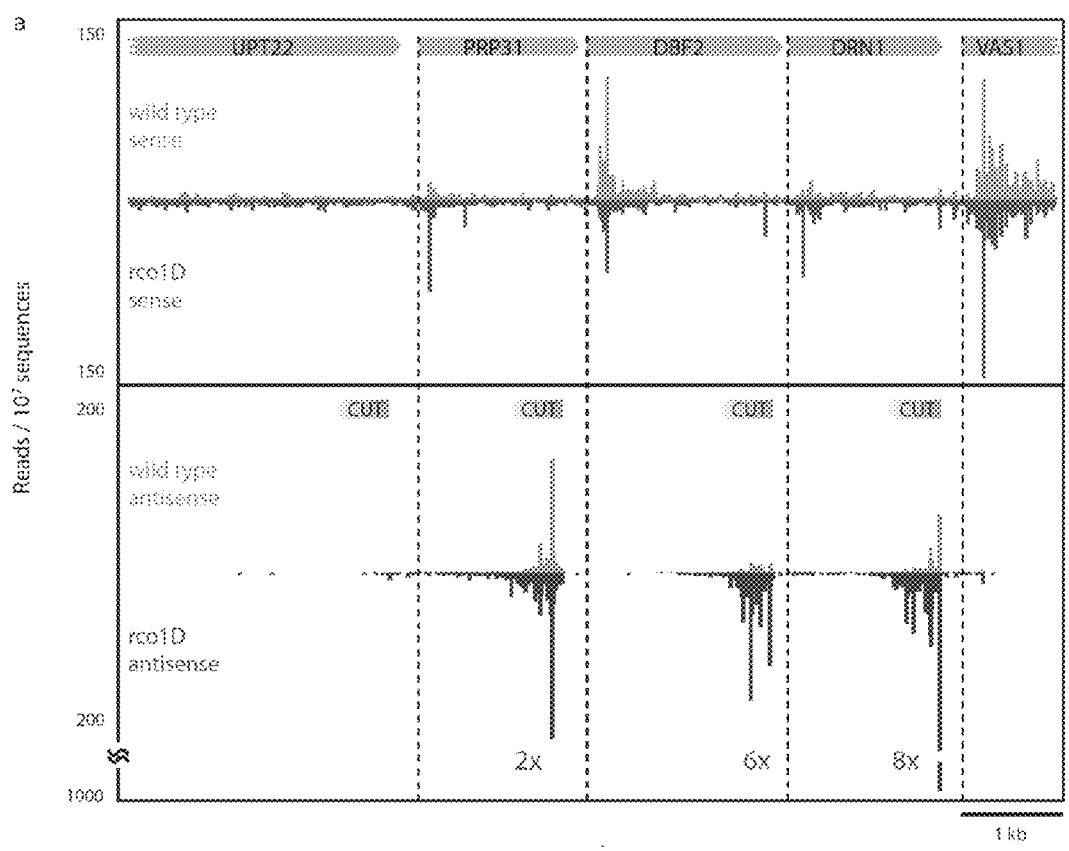
FIG. 3A-3C: Rco1 suppresses antisense transcription at divergent promoters.
Figure 3C:
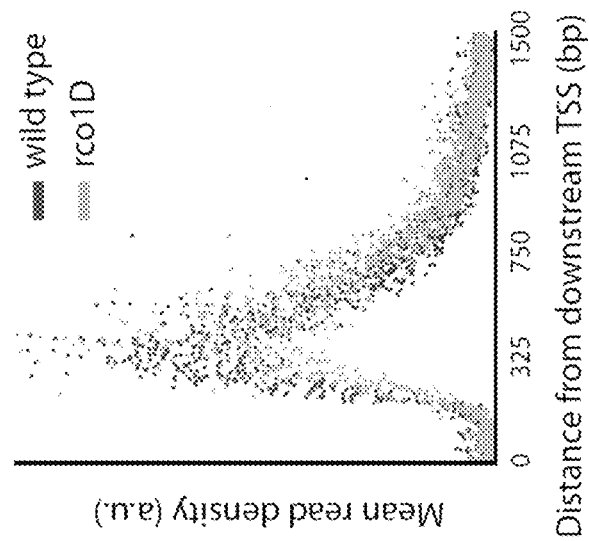
Figure 3B:
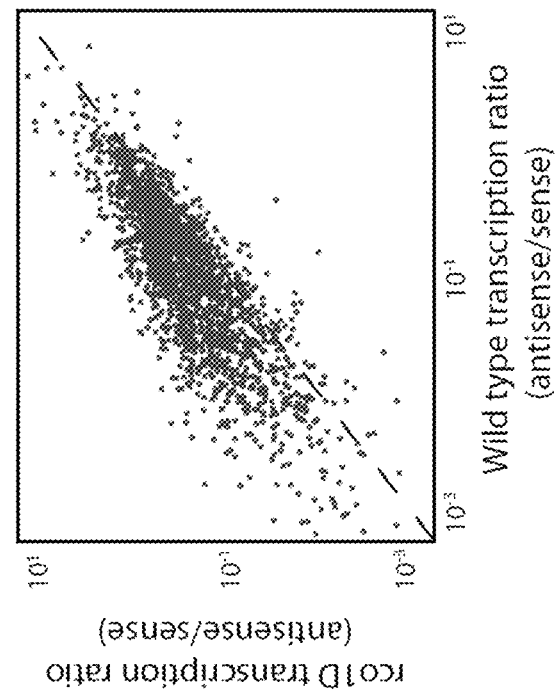

The strong correlation between antisense transcription and H4 acetylation suggests that H4 acetylation may play a causative role in facilitating antisense transcription. To test this, we examined the effect on antisense transcription of loss of RCO1, a required and dedicated subunit of the Rpd3 small (Rpd3S) H4 deacetylation complex (Carrozza, M. J. et al., *Cell* 123:581-592 (2005); Keogh, M. C. et al., *Cell* 123:593-605 (2005)). We focused on Rpd3S, as earlier studies had shown that it contributed to deacetylation of H4 in the 3' region of transcripts and the large majority of antisense transcripts overlap the 3' ends of upstream genes. Previous global studies of Rpd3S monitored accumulation of mature stable RNAs and so would not detect effects of Rco1 on transient RNA species (Carrozza, M. J. et al., *Cell* 123:581-592 (2005); Keogh, M. C. et al., *Cell* 123:593-605 (2005)). Our analysis revealed a pervasive increase (average 4-fold) in unstable antisense transcription (FIG. 3a-b). This effect was the dominant transcriptional phenotype that we observed and was specific to antisense transcription: we found no systematic increase in RNAPII density at the beginning of sense transcripts (FIGS. 9A-9D and 10). Importantly, antisense transcripts seen in the rco1 Δ strain have the same transcription start sites and the same lengths as the wild type transcripts, indicating that Rco1 is acting at the initiation stage of antisense transcription and does not affect termination (FIG. 3c). Additionally, we observed that deletion of EAF3, another subunit of Rpd3S, mimicked the increases seen in the rco1Δdata ($r_s$=0.88, FIG. 11A-11D). Thus the primary function of the Rpd3S histone deacetylase complex appears to be to enforce promoter directionality.

This raises the question of how Rpd3S is recruited to positions designated for suppression of antisense transcription. The Rco1 and Eaf3 components of the Rpd3S complex bind H3 lysine 36 methylation marks made by Set2 and that binding activates Rpd3S's deacetylase activity (Carrozza, M. J. et al., *Cell* 123:581-592 (2005); Keogh, M. C. et al., *Cell* 123:593-605 (2005); Li, B. et al., *J. Biol. Chem.* 284:7970-7976 (2009)). However, a distinct RNAPII-associated methyltransferase, Set1, has also been implicated in Rpd3S-dependent repression (Pinskaya, M. et al., *EMBO J.* 28:1697-1707 (2009)). Moreover, even in the absence of methylation, RNAPII is capable of recruiting Rpd3S to gene bodies during transcription (Govind, C. K. et al., *Mol Cell* 39:234-246 (2010)).

To investigate how Rpd3S is localized to suppress antisense transcription, we analyzed nascent transcripts in cells lacking Set1 or Set2. SET1 deletion caused a weak increase in antisense transcription in a manner that correlated only modestly with the rco1 Δ and eaf3 Δ data ($r_s$=0.36, $r_s$=0.38 respectively, FIG. 11A-11D). In contrast, deletion of SET2 led to a pronounced increased in antisense transcription that was highly correlated with the rco1 Δ and eaf3 Δ data ($r_s$=0.88, $r_s$=0.89 respectively, FIG. 11A-11D). These data together with earlier work on the Set2/Rpd3s pathway argue that the major mechanism for Rpd3S action on antisense transcription involves Set2 recruitment to elongating RNAPII via Ser2 phosphorylation on its C-terminal domain (Krogan, N. J. et al., *Mol Cell Biol* 23:4207-4218 (2003)). This in turn, through the Set2 methylation activity, allows recruitment of Rpd3S to the 3' ends of genes suppressing antisense transcription from downstream NFRs. Future challenges will be to explain how histone acetylation in the body of antisense transcripts can affect transcription initiation and to determine other mechanisms that localize Rpd3S particularly for the handful of antisense transcripts do not overlap the 3' ends of genes.

Widespread Pausing Occurs Throughout Transcription Elongation

Figure 12:
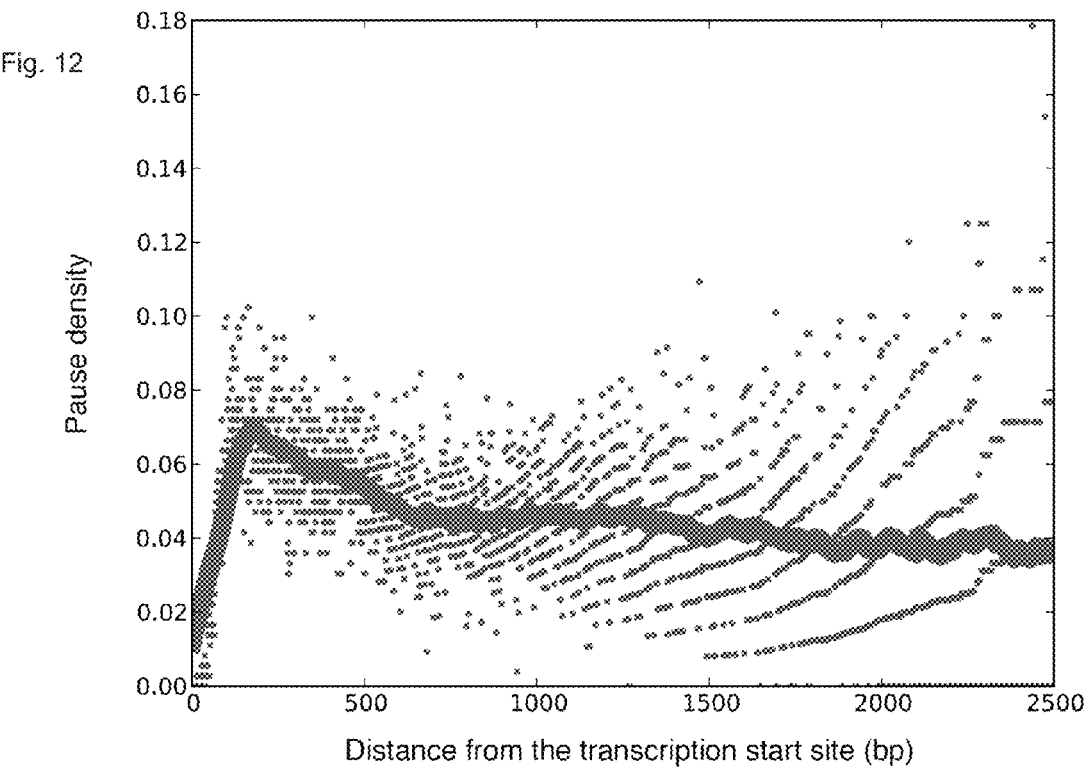
FIG. 12 Average pause density across gene bodies for highly expressed genes (N=361, >4 reads/bp).
Figure 13A:
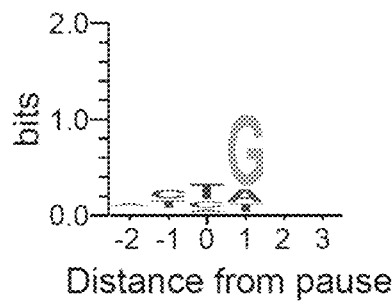
FIG. 13A-13C: Pause finding analysis on mRNA data FIG. 13A) Sequence consensus of extracted pauses in mRNA data shows a strong propensity for G's to occur at the base following the 3' end of the fragmented transcript. This bias occurred during the fragmentation of full length mRNA. After removing all pauses that are followed by a G, the average distance between pauses was measured for each gene for nascent RNA (FIG. 13B) and for fragmented mRNA (FIG. 13C).
Figure 13B:
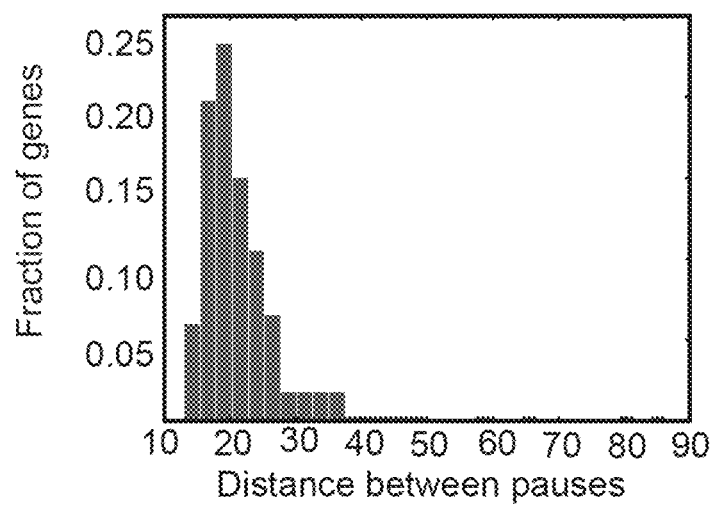
Figure 13C:
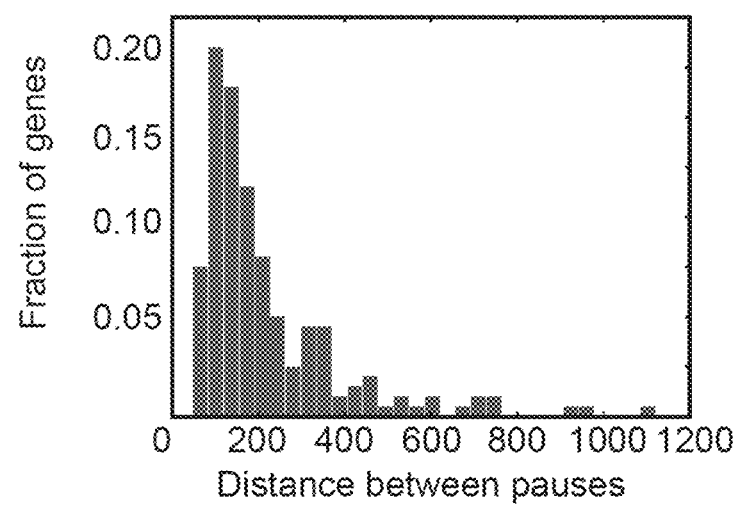

The ability of NET-seq to map the density of nascent transcripts enables in-depth investigation of the extent and sources of RNAP pausing in vivo. Our data revealed strong and highly reproducible spikes in the density of 3' ends of nascent transcripts along a given gene indicative of RNAPII pause sites (e.g. GPM1, FIG. 4a). We developed an algorithm to identify RNAPII pause positions that finds points where the read density is at least three standard deviations above the mean in a local 200 bp window. We found that pauses occur frequently throughout the body of messages and are evenly distributed after the first ~700 bp (FIG. 4b and FIG. 12). The high density of pauses was not an artifact of library generation and sequencing biases, as we detected 10-fold fewer spikes in data from mRNA lightly fragmented by alkaline hydrolysis (FIG. 13A). Dramatically, 70% of the more than $2\times10^5$ pause sites we identified had an A at the 3' end of the transcript. Additionally, there was a preference for the pause to be followed immediately by a T and then G (FIG. 4c). None of these biases were seen in the control sample of fragmented mRNA (FIG. 13A).

Largely from in vitro studies, one mechanism of RNAP pausing has been shown to involve backtracking: after encountering a blockage, RNAP reverses direction and moves upstream (Nudler, E. et al., Cell 89:33-41 (1997)). In the backtracked state, the 3' end of the RNA transcript is no longer aligned with the active site and RNAP must either return to the initial pause site or cleave the transcript. The latter option is aided by the presence of the elongation factor, TFIIS (Dst1 in yeast), that enhances RNAP's intrinsic RNA cleavage activity (FIG. 5a) (Izban, M. G. & Luse, D. S., J. Biol. Chem. 267:13647-13655 (1992); Reines, D. et al., Current Opinion in Cell Biology 11:342-346 (1999)). Although the role of TFIIS is well established in vitro, its mechanism in vivo has been less explored (Kulish, D. & Struhl, K., Mol. Cell Biol. 21:4162-4168 (2001); Nechaev, S. et al., Science 327:335-338 (2010); Sigurdsson, S. et al., Mol. Cell 38:202-210 (2010)).

Figure 5D:
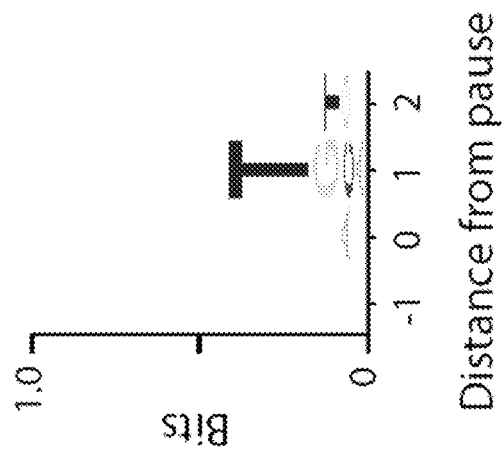
Figure 5C:
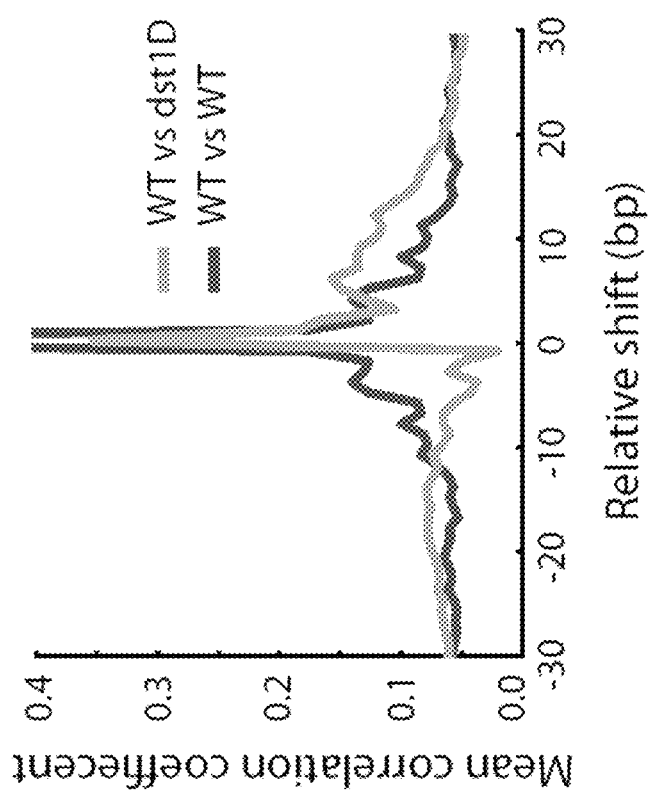

To investigate the role backtracking has in pausing in vivo, we deleted DST1 and repeated the NET-seq assay. Strikingly, we saw a large-scale downstream shift in the position of the pauses on average of 5-18 bp (FIG. 5b-c). This shift was observed for ~75% of the pauses (FIG. 14) and was accompanied by a global change in the sequences surrounding pause sites; the preference for A at the pause was lost and instead there was a strong preference for T immediately downstream of the pause (FIG. 5d). These observations confirm that the observed spikes in NET-seq data result from RNAPII pausing and indicate that pausing is followed by backtracking, which previously had been observed at promoter-proximal pauses, (Nechaev, S. et al., Science 327:335-338 (2010)) is prevalent throughout the body of transcripts. Additionally, our studies argue that Dst1-stimulated RNA cleavage has a strong sequence bias and that a slow step follows cleavage before transcription resumes.

RNAPII Pause Density Peaks Prior to the Nucleosome Dyad

The pauses observed in the dst1 Δ strain reveal positions where RNAPII began to backtrack and, therefore, represent the primary point of transcriptional blockage. By analyzing these pause positions, we can evaluate what induced RNAPII to backtrack. In vitro, nucleosomes induce RNAPII backtracking and TFIIS aids the progression of RNAPII through them (Hodges, C. et al., Science 325:626-628 (2009); Kireeva, M. L. et al., Cell 18:97-108 (2005)). In vivo, it is unknown whether nucleosomes interfere with transcription, as chromatin remodelling factors could greatly diminish the nucleosome barrier or remove nucleosomes prior to RNAPII arrival (Li, B. et al., Cell 128:707-719 (2007); Petesch, S. J. & Lis, J. T., Cell 134:74-84 (2008)). Global high-resolution measurements of steady-state nucleosome occupancy revealed that the first few nucleosomes after the transcription start site (TSS) are phased and well-positioned (Weiner, A. et al., Genome Res 20:90-100 (2010); Kaplan, N. et al., Nature 458:362-366 (2009)). Thus by correlating the relative density of RNAPII pauses with nucleosome positions, we can evaluate whether nucleosomes promote RNAPII pausing in vivo.

Figure 6:
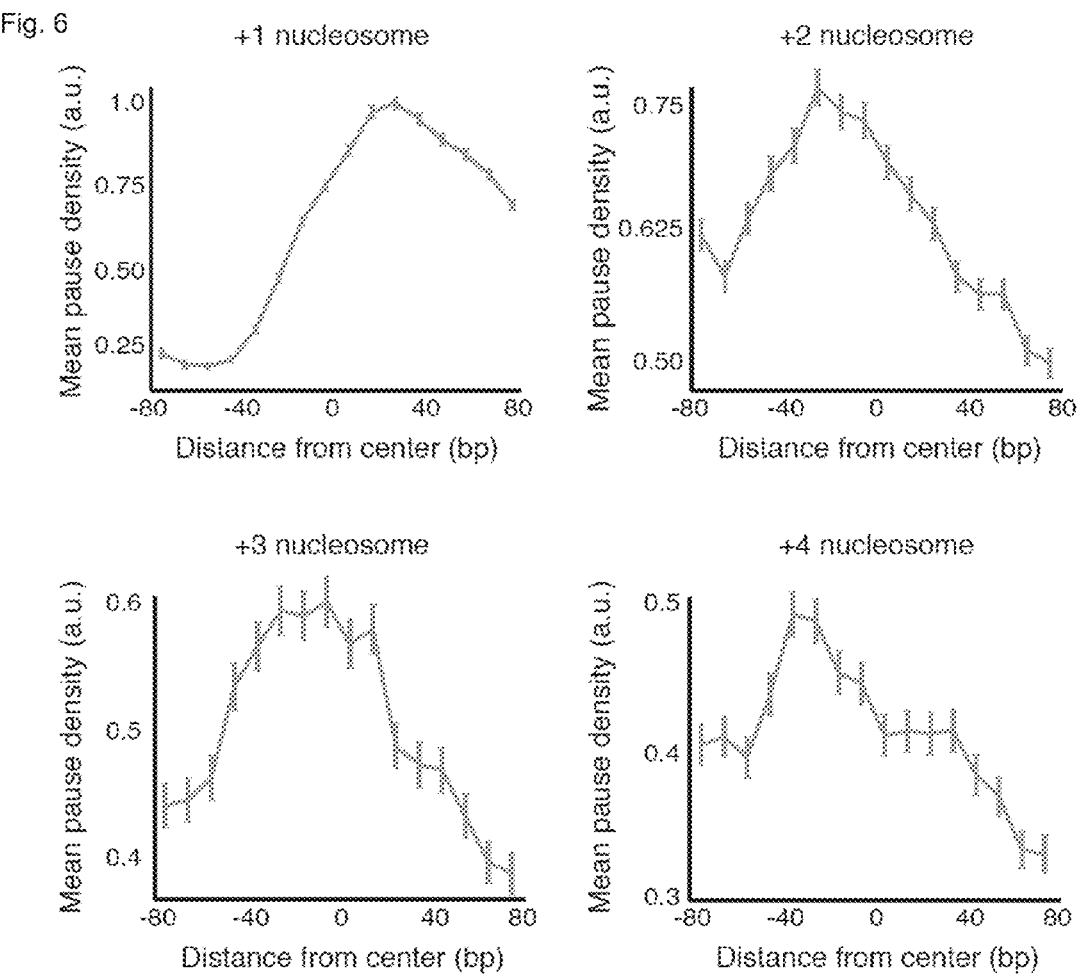
FIG. 6 Nucleosomes are a major barrier to transcription. Plot of mean pause densities in dst1 Δ data relative to the first four nucleosomes after the transcription start site using available nucleosome positioning data (Weiner, A. et al., *Genome Res* 20:90-100 (2010)). Error bars represent one standard deviation.
Figure 15:
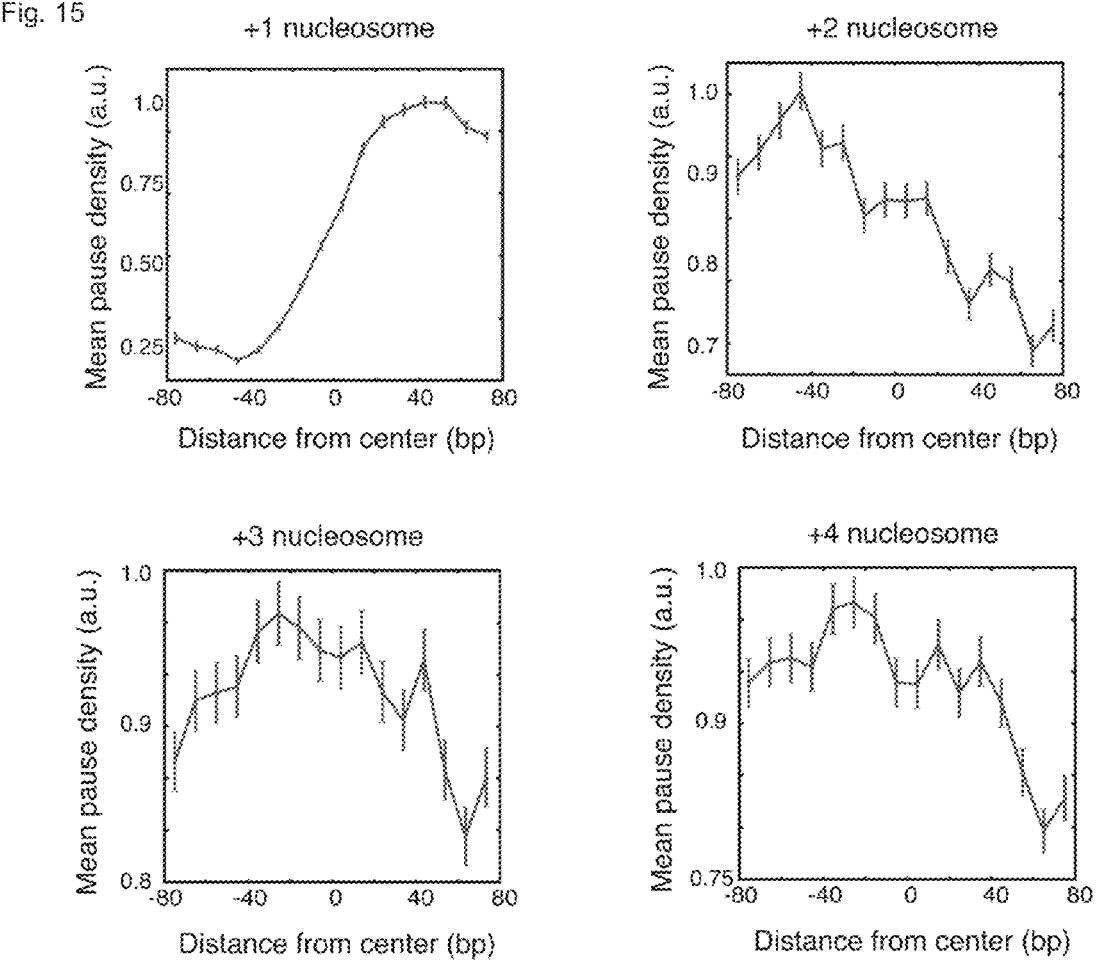
FIG. 15 Mean pause density of the wild type strain at the first four nucleosomes following transcription start sites. Error bars are placed at one standard deviation.

We compared the pause positions in the dst1 Δ strain to the centre positions of nucleosomes using previously published data (Weiner, A. et al., Genome Res 20:90-100 (2010)). Strikingly, we saw marked peaks of mean pause density at each of the first four nucleosomes (FIG. 6). The precise position of the point of maximal RNAPII pausing at the +1 nucleosome is obscured because it is located just after the TSS where many nascent transcripts are too short for unique alignment to the genome. For the +2, +3 and +4 nucleosomes, however, the pause density peaks just prior to the nucleosome dyad axis (FIG. 6). As would be expected from RNAPII backtracking, the excess pause density prior to the nucleosome dyad in the wild type strain is spread out over the upstream region (FIG. 15).

Our finding that the peak in pause density occurs just prior to the nucleosome dyad is particularly remarkable as it is in excellent agreement with earlier biophysical measurements. Specifically, optical trapping studies that physically unwrapped the DNA of a nucleosome off the histone core observed that the dyad is the point where the strongest DNA-histone contacts are found (Hall, M. A. et al., Nat. Struct. Mol. Biol. 16:124-129 (2009)). Moreover, high-resolution optical trapping experiments that followed RNAPII transcribing through a nucleosome, found that the RNAPII pause density peaked prior to the nucleosome dyad (Hodges, C. et al., Science 325:626-628 (2009)). Taken together, the above observations provide strong evidence that nucleosomes do indeed present a barrier to elongating polymerases in vivo and that this barrier leads to polymerase pausing and backtracking.

Discussion

One of the major surprises in the transcription field in recent years has been the widespread observation of divergent transcription revealing that the majority of promoters engage in canonical transcription in the sense direction along with the production of unstable transcripts in the antisense direction (Preker, P. et al., Science 322:1851-1854 (2008); Xu, Z. et al., Nature 457:1033-1037 (2009); Neil, H. et al., Nature 457: 1038-1042 (2009); Core, L. J. et al., Science 322:1845-1848 (2008); Seila, A. C. et al., Science 322:1849-1851 (2008)). NET-seq provides an ideal tool to look at this phenomenon revealing several fundamental properties of divergent transcription. First, most promoters show a strong directionality favoring the sense transcript. Second, suppression of antisense transcripts is enforced by two distinct mechanisms: Rpd3S-mediated deacetylation which prevents antisense initiation and an independent mechanism, previously characterized to involve the Nrd1-Nab3-Sen1 complex (Arigo, J. T. et al., Mol. Cell 23:841-851 (2006)), that terminates antisense transcripts and shuttles them to exosome-mediated degradation. Interestingly, sense transcription may also use this termination mechanism as our data showed an enrichment for transcripts at the 5' end of genes that mirrors what we observed for antisense transcripts and complements observations that Nrd1 localizes to the 5' end of genes (Vasiljeva, L. et al., Nat. Struct. Mol. Biol. 15:795-804 (2008)). Third, our observations suggest an independence between the initiation of the sense and antisense transcripts. Specifically, we found only modest correlation between sense and antisense transcription levels. Moreover, even among the set of antisense transcripts that increased when RCO1 is deleted, no increase in sense transcription levels was seen. These findings argue against models in which antisense transcription serves to promote sense transcription (e.g., by unwinding DNA supercoils or by removing nucleosomes.)

The potential for RNAP to pause has been apparent for decades motivating interest in the mechanisms and regulatory roles of pausing in the transcription field (Kassayetis, G. A. & Chamberlin, M. J., *J Biol Chem* 256:2777-2786 (1981); Herbert, K. M. et al., *Cell* 125:1083-1094 (2006); Kireeva, M. L. & Kashlev, M., *Proc. Natl. Acad. Sci. USA* 106:8900-8905 (2009); Kireeva, M. L. et al., *Cell* 18:97-108 (2005); Core, L. J. et al., *Science* 322:1845-1848 (2008)). NET-seq provides the first in-depth view of pausing in a eukaryotic cell revealing that transcription is punctuated by pauses throughout the body of all messages. Taking into account both the abundance and magnitude of the pauses, we conclude that RNAPII spends comparable time in a paused state and moving forward (FIG. 16). We establish that nucleosomes induce pausing in vivo, and may be the major source of pausing considering that the increase in pause density at nucleosomes is comparable to the increase in nucleosome occupancy (Weiner, A. et al., *Genome Res* 20:90-100 (2010)). Our observation that pausing peaks at the nucleosome dyad reveal a striking similarity between our measurements and optical trap measurements arguing that the physical forces observed in purified in vitro systems are at play in the cell. NET-seq's ability to follow the physical basis of transcription in vivo allowing direct comparison with high resolution in vitro measurements may prove to be the most transformative aspect of this approach.

Methods

Nascent RNA Purification.

All experiments were conducted using derivatives of yeast strain BY4741. Epitope-tagged Rpb3 (C-terminal 3×FLAG) was expressed from its endogenous locus. Deletion strains were made by standard PCR-based methods. Liters of log phase culture in YEPD were harvested by filtration and flash frozen by plunging into $lN_2$. Frozen cells were lysed cryogenically via six cycles of pulverization using a mixer mill.

Clarified and DNAse I digested lysate was added to washed ANTI-FLAG M2 Affinity Gel (Sigma Aldrich), incubated at 4° C. and nutated for 2.5 hours. After washing, bound proteins were eluted twice with 2 mg ml$^{-1}$ 3× Flag peptide (Sigma Aldrich). RNA from the eluates was purified using the miR-Neasy kit (Qiagen).

DNA Linker Ligation, cDNA Synthesis and PCR.

A DNA linker (5'-CTGTAGGCACCATCAAT (SEQ ID NO:1)) which was 5' adenylated (i.e. modified at the 5'-end by bonding to the pyrophosphate moiety of adenosine 5'-pyrophosphate), and blocked at the 3'-end with a dideoxy-C base (SEQ ID NO:11), Integrated DNA Technologies, was ligated onto the 3' end of the immunoprecipitated RNA based on previous described strategy (Unrau, P. J. & Bartel, D. P., *Nature* 395:260-263 (1998)). Ligation conditions (see below) were systematically optimized to maximize ligation efficiency to ~90% to ensure that the majority of the input RNA was ligated avoiding any bottleneck biases.

cDNA synthesis and sequencing was performed as described with a few modifications (Ingolia, N. T. et al., *Science* 324:218-223 (2009)). The sequencing primer binding site was positioned so that sequencing would start at the 3' end.

Comparing Pause Densities to Nucleosome Positions.

Nucleosome positions (Weiner, A. et al., *Genome Res* 20:90-100 (2010)) were assigned as +1, +2, +3, etc., according to their position relative to transcription start sites. The pause density relative to a particular nucleosome was determined by the number of pauses observed at that position divided by the total number of opportunities it could be observed there.

$$\text{Mean Density}_k(x) = \left(\frac{N_p}{N_o}\right)_x = \frac{\sum_i^{\text{all genes}} g_i(y)}{\sum_i^{\text{genes with TSS}<y} 1}$$

$$y = n_i^k x$$

where k is the nucleosome number, g(y) is the binary function indicating whether a pause occurs at y and $n_i^k$ are the centre nucleosome positions. The error of the pause density was calculated via the standard deviation of the binomial distribution, $$\frac{\sqrt{N_p(1 - N_p/N_o)}}{N_o}$$

Strain Construction.

All experiments were conducted using derivatives of yeast strain BY4741. Epitope-tagged Rpb3 (C-terminal 3×FLAG) was expressed from its endogenous locus. Deletion strains were made by standard PCR-based methods.

Extract and Total RNA Preparation.

Yeast strains were grown in YEPD at 30° C. with shaking from an initial OD of 0.1 to mid-log phase with an OD of 0.6-0.8. Two liters of yeast culture were harvested in turn by filtration onto 0.45 um pore size nitrocellulose filters (Whatman). The culture was scrapped off the filter with a spatula pre-chilled by $lN_2$ and flash frozen by plunging into $lN_2$. Frozen cells were pulverized for six cycles, each of 3 min. at 15 Hz, on a Retsch MM301 mixer mill. Sample chambers were pre-chilled in $lN_2$ and re-chilled between each pulverization cycle.

One gram of ground cells (~1 liter at 0.7 OD) was added to 5 mL of ice cold lysis buffer (20 mM Hepes, pH 7.4, 110 mM KOAc, 0.5% Triton X-100, 0.1% Tween 20, 10 mM $MnCl_2$, 50 U mL$^{-1}$ SUPERase•In (Ambion)) supplemented with protease inhibitor cocktail (1× Complete, EDTA-free, Roche)). The experiment using α-amanitin included 10 μg mL$^{-1}$ α-amanitin (Sigma Aldrich) in the lysis buffer. After resuspending the lysate by pipetting, 660 units of DNAse I (Promega, RQ1 RNase-Free DNase) was added and incubated for 20 minutes on ice. The lysate was then clarified by centrifugation at 4° C. at 20000×g for 10 minutes. The supernatant is reserved for immunoprecipitation.

200 μL of clarified lysate is reserved for total RNA purification which was done by the hot acid phenol method. Typical yields were 20 μg.

Native Affinity Purifications of RNAPII.

0.5 mL of ANTI-FLAG M2 Affinity Gel (Sigma Aldrich) was washed twice with lysis buffer. The clarified lysate was added to the washed gel, incubated at 4° C. and nutated for 2.5 hours. The immunoprecipitation was washed 4×10 mL with wash buffer (20 mM Hepes, pH 7.4, 110 mM KOAc, 0.5% Triton X-100, 0.1% Tween 20, 50 U/mL SUPERase•In (Ambion)), 1 mM EDTA). Bound proteins were eluted twice with 150 μl elution buffer (20 mM Hepes, pH 7.4, 110 mM KOAc, 0.5% Triton, 0.1% Tween) with 2 mg ml$^{-1}$ 3× Flag peptide (Sigma Aldrich). RNA from the combined eluates was purified using the miRNeasy kit (Qiagen, 217004). A typical yield from approximately one liter of log-phase yeast culture was 3 μg.

mRNA Purification and Fragmentation.

Polyadenylated mRNA was purified from 50 μag total RNA using magnetic oligo-dT DynaBeads (Invitrogen). Purified RNA was eluted in 20 μl 10 mM Tris, pH 7.0. The purified mRNA was mixed with an equal volume of 2× alkaline fragmentation solution (2 mM EDTA, 10 mM $Na_2CO_3$, 90 mM $NaHCO_3$, pH≈9.3) and incubated for 5 minutes at 95° C. These conditions yielded lightly fragmented RNA of size distribution similar to that of the nascent RNA. The fragmentation reaction was stopped by addition 0.56 mL of ice-cold precipitation solution (final 300 mM NaOAc pH 5.5, plus GlycoBlue (Ambion) as a coprecipitant), RNA was purified by a standard isopropanol precipitation as follows. After adding 650 μL of isopropanol, samples were placed at −30° C. for at least 30 minutes. Precipitated RNA was pelleted by centrifugation at 4° C. at 20000×g for 30 minutes. The pellet was air dried after a quick wash with 80% ethanol and then resuspended in 10 mM Tris pH 7.0.

6.4 μg of fragmented mRNA was dephosphorylated in a 50 μL reaction with 1×T4 polynucleotide kinase buffer without ATP, 0.5 U SUPERase•In (Ambion) and 22.5 units T4 polynucleotide kinase (NEB). The dephosphorylation reaction was incubated at 37° C. for 1 hour followed by 10 min at 75° C. for enzyme heat inactivation. RNA was precipitated with GlycoBlue by standard methods (see above).

DNA Linker Ligation, Fragmentation and Size Selection.

A DNA linker (SEQ ID NO:11) was ligated onto the 3' end of the immunoprecipitated RNA, the fragmented mRNA and a synthetic 28 base RNA oligonucleotide (oNT1199, 5'-AUGUACACGGAGUCGACCCGCA ACGCGA (SEQ ID NO:2)) similarly to what has been described (Unrau, P. J. & Bartel, D. P., *Nature* 395:260-263 (1998)). Specifically, 3 μg of each RNA sample was broken into 3 reactions and diluted to 10 μL with 10 mM Tris, pH 7.0. After a brief denaturation the reactions were brought to 20 μL with a buffer that gave final concentrations of 12% PEG8000, 50 ng μl$^{-1}$ linker, 1×T4 Rnl2, truncated reaction buffer and 2 units μl$^{-1}$ of T4 Rnl2, truncated (NEB). The reaction was incubated at 37° C. for 3 hours. Ligation conditions were systematically optimized to maximize ligation efficiency to ~90% to ensure that the majority of the input RNA was ligated.

Fragmentation of the ligated samples allowed for the final DNA library to contain inserts of a narrow range to reduce any length biases of downstream enzymatic reactions. EDTA was added to all reactions for a final concentration of 17 mM. 20 μL of 2× alkaline fragmentation solution (2 mM EDTA, 10 mM $Na_2CO_3$, 90 mM $NaHCO_3$, pH≈9.3) was added to each reaction and incubated at 95° C. for 30 minutes. The reactions were stopped by addition 0.56 mL of ice-cold precipitation solution (final 300 mM NaOAc pH 5.5, plus GlycoBlue (Ambion) as a coprecipitant), followed by a standard isopropanol precipitation (see above).

The ligated and fragmented samples were size-selected by gel electrophoresis. The purified reactions along with the oNTI199 RNA oligo was mixed with 2× Novex TBE-Urea sample prep buffer (Invitrogen) and briefly denatured, then loaded on a Novex denaturing 15% polyacrylamide TBE-urea gel (Invitrogen) and run according to the manufacturer's instructions. The gel was stained with SYBR Gold (Invitrogen) and the 35-85 nt region was excised. The gel was physically disrupted and either allowed to soak overnight in gel elution buffer (300 mM NaOAc pH 5.5, 1 mM EDTA, 0.1 U μl$^{-1}$ SUPERase•In) or incubated in 200 μL of DEPC water for 10 min at 70° C. The gel debris was removed from the water or buffer using a Spin-X column (Corning) and RNA was precipitated with GlycoBlue as a coprecipitant using standard methods.

cDNA Synthesis.

cDNA synthesis was performed as described with a few modifications (Ingolia, N. T. et al., *Science* 324:218-223 (2009)). The primer used for reverse transcription was oLSC003 (5' pTCGTATGCCGTCTTCTGCTTG (SEQ ID NO:3)•AATGATACGGCGACCACCGATCCGAC-GATCATTGATGGTGCCTACAG (SEQ ID NO:4)) where the initial p indicates 5' phosphorylation and • indicates a spacer, 18 carbon spacer-CACTCA-18 carbon spacer. Efficient circularization of the RT product was performed as described (Ingolia, N. T. et al., *Science* 324:218-223 (2009)) with CircLigase (Epicentre) according to the manufacturer's directions. Any ligation bias at this step is averaged out as the random fragmentation leaves a range of 5' ends for each 3' end. The PCR was performed directly on the circularized product as described (Ingolia, N. T. et al., *Science* 324:218-223 (2009)) resulting in DNA with Illumina cluster generation sequences on each end and a sequencing primer binding site positioned so that sequencing would start at the 3' end. DNA was purified from a PCR reaction that had not reached saturation and was quantified using the Agilent BioAnalyzer High Sensitivity DNA assay. DNA was then sequenced on the Illumina Genome Analyzer 2 according to the manufacturer's instructions, using 4 to 6 pM template for cluster generation and sequencing primer oLSC006 (5'-TCCGACGATCAT-TGATGGTGCCTACAG (SEQ ID NO:5)).

Data Analysis:

Data analysis was performed using scripts written in Python 2.6 that are available upon request.

Sequencing Analysis.

Image data obtained by the Illumina Genome Analyzer 2 was analyzed using the GAPipeline to extract raw sequences. Matrix and phasing parameters were estimated from a φX control lane.

Sequence Alignment.

Raw sequences 40 bases long were composed of the cDNA of the fragmented RNA sequence. For RNA fragments smaller than 40 bases, the sequence is followed by part of the 5' Illumina linker sequence which was removed in silico. Alignments to the yeast genome was performed by the alignment program, Bowtie 0.12.0[44] (http://bowtie-bio.sourceforge.net/). Bowtie settings were chosen so that three mismatches were allowed and alignments were required to be unique. The shortest sequenced fragments were approximately 18 nucleotides due to the RNA size selection step after ligation and random fragmentation. 18 bp sequences would occur by chance every 6.9 e+10 bp which is sufficiently rare for 18 bp sequences to be generally uniquely aligned to the 1.2 e+7 bp yeast genome. Alignments were first performed against tRNA and rRNA sequences to remove them. The remaining sequences were aligned against a recent version of the yeast genome downloaded from the *Saccharomyces* Genome Database (SGD, http://www.yeastgenome.org/) on Oct. 11, 2009. Statistics on sequence alignments are reported in Table 1.

Quantifying Antisense and Sense Transcription Levels.

At tandem promoters sense transcription was determined using available annotated transcription start sites (TSS) (Xu, Z. et al., *Nature* 457:1033-1037 (2009)). To allow for the error involved in these TSS measurements, we calculated the sum of the read density in 500 nucleotide windows for the first 700 bases after the TSS and chose the highest sum. The antisense transcription was determined by starting 100 bases upstream of the TSS and the read density sum in 500 nucleotide wide windows was calculated for the subsequent 1000 bases. The highest sum was used for downstream analysis.

Metagene Analysis.

Each gene included in the analysis is normalized by the mean number of reads in a 400 bp window beginning 100 bases downstream from the transcription start site. A mean read density (MRD) is then calculated for each position over all genes as described below.

$$MRD(i) = \frac{\sum_{j}^{all\ genes}\left(\frac{r_i^j}{\sum_{i=100}^{500} r_i^j / 400}\right)}{\sum_{j}^{all\ genes} 1}$$

where $r_i^j$ are the reads for the $j^{th}$ gene at the $i^{th}$ position after the transcription start site.

Extracting Pause Positions.

Pauses were identified in previously annotated transcription units (Xu, Z. et al., *Nature* 457:1033-1037 (2009)) of well-expressed genes. Pauses were defined as having reads higher than three standard deviations above the mean of the surrounding 200 nucleotides which do not contain pauses. Pauses were required to have at least four reads regardless of the gene's sequencing coverage. Sequence consensus was calculated by WebLogo 3 (http://weblogo.threepluso-ne.com/) (Crooks, G. E. et al., *Genome Res* 14:1188-1190 (2004)).

Comparing Pause Densities to Nucleosome Positions.

Nucleosome positions (Weiner, A. et al., *Genome Res* 20:90-100 (2010)) were assigned as +1, +2, +3, etc., according to their position relative to transcription start sites. The mean pause density (MPD) relative to a particular nucleosome was determined by the number of pauses observed at that position divided by the total number of opportunities it could be observed there.

$$MRD_k(x) = \left(\frac{N_p}{N_o}\right)_x = \frac{\sum_{i}^{all\ genes} g_i(y)}{\sum_{i}^{genes\ with\ TSS < y} 1}$$

$$y = n_i^k x$$

where k is the nucleosome number, g(y) is the binary function indicating whether a pause occurs at y and $n_i^k$ are the centre nucleosome positions. For the +2 and +3 nucleosomes, the number of pause opportunities was uniform at every position and was simply the number of genes included in the analysis. The +1 nucleosome analysis required that the number of pause opportunities at each position represent the number of genes where that position occurs after the transcription start site. The error of the pause density was calculated via the standard deviation of the binomial distribution, $$\frac{\sqrt{N_p(1 - N_p/N_o)}}{N_o}$$

The densities were then binned by averaging across windows ten nucleotides wide. The error for each bin was calculated by computing the sum of the variances of the binned measurements and calculating the square root.

Western Blot.

Proteins were transferred from SDS-PAGE gels to nitrocellulose membranes and probed for FLAG-labelled proteins by using standard western blot procedures with rabbit anti-Flag (Sigma Aldrich). Western blots were scanned using an Odyssey fluorescent scanner (Li-Cor Biosciences).

qPCR Analysis of the Immunoprecipitation Specificity.

Strains expressing GFP did so by overexpression on a 2-micron plasmid from a pTEF2 promoter. ~100 ng of RNA eluted from the RNAP II immunoprecipitation (IP) was treated with DNAse I (Promega) according to the manufacturer's instructions. The GFP and TDH3 transcripts in the DNAse-treated RNA from the IP and the total RNA were converted to cDNA by reverse transcription using SuperScript III (Invitrogen) according to the manufacturer's instructions. GFP and TDH3 RT primers were 5' GTCATGC-CGTTTCATATGATCTGGG (SEQ ID NO:6) and 5' GGGTCTCTTTCTTGGTAAGTAGCAATC (SEQ ID NO:7) respectively. qPCR reactions were set up using EXPRESS SYBR GreenER qPCR SuperMix Universal (Invitrogen) according to the manufacturer's instructions and for a series of cDNA template dilutions. TDH3 qPCR primers were 5' GTTGCTTTGAACGACCCATT (SEQ ID NO:8) and 5' GGGTCTCTTTCTTGGTAAGTAGCAATC (SEQ ID NO:7). GFP qPCR primers were 5' CTGGAGTTGTC-CCAATTCTTG (SEQ ID NO:9) and 5' GTTGGCCATG-GAACAGGTAG (SEQ ID NO:10). Detection of the PCR reaction was done by a continuous fluorescence detector (DNA Engine Opticon, MJ Research). Data analysis occurred as described (Livak, K. J. & Schmittgen, T. D., *Methods* 25:402-408 (2001)), however, the differential amplification efficiencies of TDH3 and GFP were measured and accounted for.

TABLE 1

Alignment statistics.
The total number of reads for each sample and the number of reads that align to tRNA, rRNA and genomic DNA followed by the percentage of each. With these statistics we estimated the amount of enrichment for nascent RNA that occurred during the RNAP II immunoprecipitation. Considering that the median lifetime of mRNA in yeast is 20 minutes (Wagner, A., *Mol. Biol. Evol.*, 22: 1365-1374 (2005)), the expected concentration of nascent RNA is [nascent RNA] = (ln(2)/20) * [mature RNA]. As mRNA constitutes approximately 5% of the total RNA in a yeast cell (Warner, J. R., *Trends Biochem. Sci.* 24: 437-440 (1999)), we expect nascent RNA to be 0.34% of the total RNA. Alignments to genomic regions represented 27%-42% of our total reads, thus the IP provided an approximately 100-fold enrichment for nascent RNA consistent with the direct measurement of enrichment made in our mixed lysate experiment (Table 2).

| Alignment | WT nascent 1 | | WT mRNA | | WT nascent 2 | |
|---|---|---|---|---|---|---|
| Total | 51,174,644 | | 51,079,222 | | 6,935,019 | |
| tRNA | 1,225,423 | 2.39 | 162,182 | 0.32 | 138,477 | 2.00 |
| rRNA | 27,999,648 | 54.71 | 30,781,359 | 60.26 | 4,202,538 | 60.60 |
| genomic | 19,395,914 | 37.90 | 17,653,868 | 34.56 | 1,877,403 | 27.07 |

| Alignment | WT nascent α-amanitin | | Δrco1 nascent | | Δdst1 nascent | |
|---|---|---|---|---|---|---|
| Total | 12,105,338 | | 18,796,881 | | 29,652,801 | |
| tRNA | 137,260 | 1.13 | 600,024 | 3.19 | 933,844 | 3.15 |
| rRNA | 6,054,585 | 50.02 | 9,338,864 | 49.68 | 17,659,127 | 59.55 |
| genomic | 5,175,283 | 42.75 | 7,812,384 | 41.56 | 9,588,097 | 32.33 |

TABLE 2

Demonstration that IP conditions are strongly specific by two control IPs. The first IP used a mixed lysate of two strains: a strain endogenously expressing a FLAG-labelled Rpb3 and a strain expressing the wild type allele of Rpb3 and an ectopically expressed gene (GFP). The second IP was performed on lysate from a strain expressing both FLAG-labeled Rpb3 and GFP. qPCR on the RNA that co-purified from each IP quantified the TDH3:GFP ratio which is summarized in the table. As the first IP had half the amount of labeled Rpb3 than the second IP, these results show that messages expressed in the same cells as a labeled Rpb3 are purified at least 100-fold more than messages from other cells.

|  | IP 1 | IP 2 |
| --- | --- | --- |
| GFP (a.u.) | 0.02 | 6.23 |
| TDH3 (a.u.) | 43.70 | 62.85 |
| TDH3/GFP | 0.00048 | 0.10 |
| IP 1/IP 2 | 207.03 | |

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method of identifying a cellular nascent RNA transcript, comprising:
   (a) arresting transcription in a cell;
   (b) purifying a native cellular nascent RNA transcript; and
   (c) sequencing said native cellular nascent RNA transcript thereby identifying the cellular nascent RNA transcript;
   wherein said native cellular nascent RNA transcript is purified as part of an RNA polymerase complex, wherein said cellular nascent RNA transcript does not comprise a labeled nucleotide and wherein said cellular nascent RNA transcript is not crosslinked to an RNA polymerase complex.

2. The method of claim 1, wherein said sequencing is performed starting at a 3'-end of said native cellular nascent RNA transcript.

3. The method of claim 1, wherein said sequencing comprises reverse transcribing said native cellular nascent RNA transcript into a DNA transcript.

4. The method of claim 1, wherein the native cellular nascent RNA transcript is sequenced by a deep sequencing method.

5. The method of claim 1, wherein the native cellular nascent RNA transcript is sequenced by a pyrosequencing method, a Sanger sequencing method, an SBS sequencing method, or a HANS sequencing method.

6. The method of claim 1, wherein the arresting comprises lowering the temperature of the cell to 10° C. or below.

7. The method of claim 6, wherein the arresting comprises contacting the cell with liquid nitrogen thereby forming a flash-frozen cell.

8. The method of claim 1, wherein the purifying comprises contacting the RNA polymerase complex with a DNAse thereby removing the DNA template.

9. The method of claim 8, wherein said one or more RNA polymerase complex proteins is an RNA polymerase.

10. The method of claim 1, wherein the native cellular nascent RNA transcript is an unstable transcript.

11. The method of claim 1, wherein the native cellular nascent RNA transcript is a sense transcript.

12. The method of claim 1, wherein the native cellular nascent RNA transcript is an antisense transcript.

13. The method of claim 1, wherein the cell is a prokaryotic cell.

14. The method of claim 1, wherein the cell is a eukaryotic cell.

15. The method of claim 14, wherein the cell is a human cell.

16. The method of claim 14, wherein the cell is a cancer cell.

17. The method of claim 1, wherein the RNA polymerase complex is derived from a virus.

18. The method of claim 1, wherein the cell is subject to a stimulus prior to arresting.

19. The method of claim 18, wherein the stimulus is a small molecule.

20. The method of claim 18, wherein the stimulus is an inhibitory nucleic acid.

21. The method of claim 18, wherein the stimulus is a protein molecule.

* * * * *

SEQUENCE LISTING

```
<160> NUMBER OF SEQ ID NOS: 11

<210> SEQ ID NO 1
<211> LENGTH: 17
<212> TYPE: DNA
<213> ORGANISM: Artificial Sequence
<220> FEATURE:
<223> OTHER INFORMATION: Synthetic DNA polynucleotide

<400> SEQUENCE: 1
ctgtaggcac catcaat                                                        17

<210> SEQ ID NO 2
<211> LENGTH: 28
<212> TYPE: RNA
<213> ORGANISM: Artificial Sequence
<220> FEATURE:
<223> OTHER INFORMATION: Synthetic RNA polyribonucleotide

<400> SEQUENCE: 2
auguacacgg agucgacccg caacgcga                                            28

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(1)
<223> OTHER INFORMATION: 5' t modified by phosphorylation
<220> FEATURE:
<221> NAME/KEY: misc_feature
<222> LOCATION: (21)..(21)
<223> OTHER INFORMATION: 3' g modified by spacer attached to SEQ ID NO:4

<400> SEQUENCE: 3
tcgtatgccg tcttctgctt g                                                   21
```

```
<210> SEQ ID NO 4
<211> LENGTH: 47
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(1)
<223> OTHER INFORMATION: 5' a modified by spacer to SEQ ID NO:3

<400> SEQUENCE: 4
aatgatacgg cgaccaccga tccgacgatc attgatggtg cctacag          47

<210> SEQ ID NO 5
<211> LENGTH: 27
<212> TYPE: DNA
<213> ORGANISM: Artificial Sequence
<220> FEATURE:
<223> OTHER INFORMATION: Synthetic DNA polynucleotide

<400> SEQUENCE: 5
tccgacgatc attgatggtg cctacag                                27

<210> SEQ ID NO 6
<211> LENGTH: 25
<212> TYPE: DNA
<213> ORGANISM: Artificial Sequence
<220> FEATURE:
<223> OTHER INFORMATION: Synthetic DNA polynucleotide

<400> SEQUENCE: 6
gtcatgccgt tcatatgat ctggg                                   25

<210> SEQ ID NO 7
<211> LENGTH: 27
<212> TYPE: DNA
<213> ORGANISM: Artificial Sequence
<220> FEATURE:
<223> OTHER INFORMATION: Synthetic DNA polynucleotide

<400> SEQUENCE: 7
gggtctcttt cttggtaagt agcaatc                                27

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA polynucleotide

<400> SEQUENCE: 8
gttgctttga acgacccatt                                        20

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA polynucleotide

<400> SEQUENCE: 9
ctggagttgt cccaattctt g                                      21
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic DNA polynucleotide

<400> SEQUENCE: 10
gttggccatg gaacaggtag                                                 20

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(1)
<223> OTHER INFORMATION: 5' c modified by adenosine pyrophosphate
<220> FEATURE:
<221> NAME/KEY: misc_feature
<222> LOCATION: (18)..(18)
<223> OTHER INFORMATION: n is dideoxy cytidine

<400> SEQUENCE: 11
ctgtaggcac catcaatn                                                   18
```